(12) United States Patent
Kato et al.

(10) Patent No.: US 6,355,152 B1
(45) Date of Patent: *Mar. 12, 2002

(54) GAS SENSOR AND NITROGEN OXIDE SENSOR

(75) Inventors: Nobuhide Kato, Ama-Gun; Kunihiko Nakagaki, Nagoya, both of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/348,857

(22) Filed: Jul. 7, 1999

(30) Foreign Application Priority Data

Jul. 8, 1998 (JP) ............................................. 10-192902

(51) Int. Cl.$^7$ ............................................. G01N 27/407
(52) U.S. Cl. ........................ 204/425; 204/426; 204/427; 205/781
(58) Field of Search ................................. 204/421–429

(56) References Cited

U.S. PATENT DOCUMENTS

| | | | |
|---|---|---|---|
| 4,324,632 A | * 4/1982 | Tantram et al. | 204/415 |
| 4,450,065 A | * 5/1984 | Yamada et al. | 204/426 |
| 4,498,968 A | * 2/1985 | Yamada et al. | 204/426 |
| 4,990,235 A | * 2/1991 | Chujo | 204/426 |
| 5,194,135 A | * 3/1993 | Hayakawa et al. | 204/426 |
| 5,314,604 A | * 5/1994 | Friese et al. | 204/426 |
| 5,763,763 A | 6/1998 | Kato et al. | |

FOREIGN PATENT DOCUMENTS

| | | |
|---|---|---|
| EP | 0 769 693 | 4/1997 |
| JP | 8-271476 | 10/1996 |
| JP | 9-113484 | 5/1997 |

\* cited by examiner

Primary Examiner—T. Tung
(74) Attorney, Agent, or Firm—Burr & Brown

(57) ABSTRACT

Disclosed are a gas sensor and a nitrogen oxide sensor each comprising a first diffusion rate-determining section for giving a predetermined diffusion resistance to a measurement gas to be introduced into a first chamber, the first diffusion rate-determining section being formed with a slit having a laterally extending aperture formed at a front end portion of a second spacer layer to make contact with the lower surface of a second solid electrolyte layer in which the aperture is formed to extend with an identical aperture width up to the first chamber, and a slit having a laterally extending aperture formed at a front end portion of the second spacer layer to make contact with the upper surface of a first solid electrolyte layer in which the aperture is formed to extend with an identical aperture width up to the first chamber. The slits have a substantially identical cross-sectional configuration, in which the length in the vertical direction is not more than 10 $\mu$m, and the length in the lateral direction is about 2 mm. Accordingly, it is possible to avoid the influence of the pulsation of the exhaust gas pressure generated in the measurement gas, and it is possible to improve the measurement accuracy obtained on the detecting electrode.

10 Claims, 34 Drawing Sheets

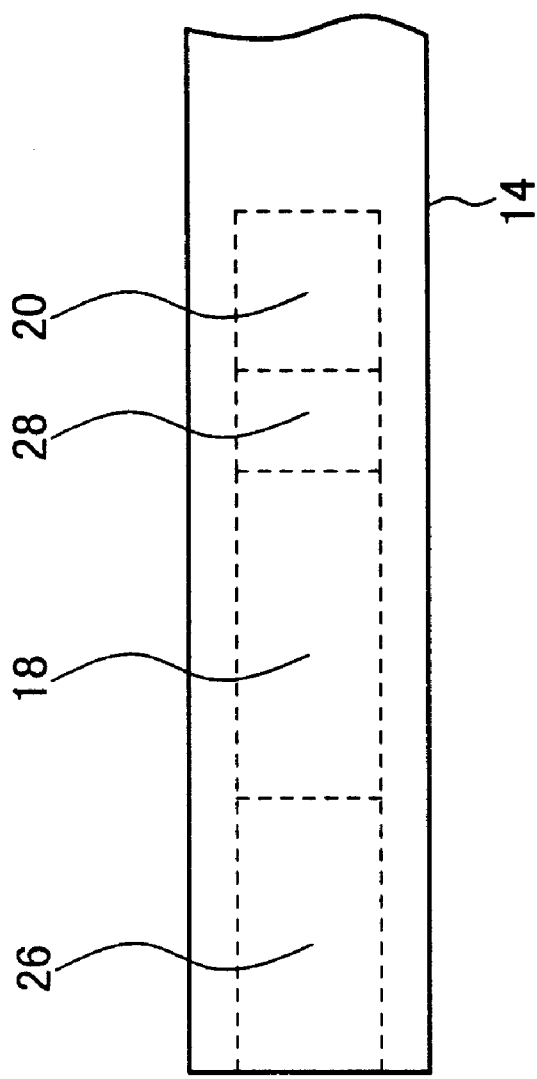
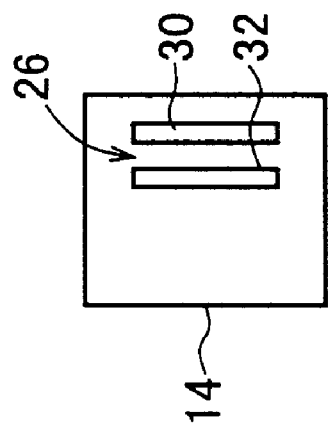

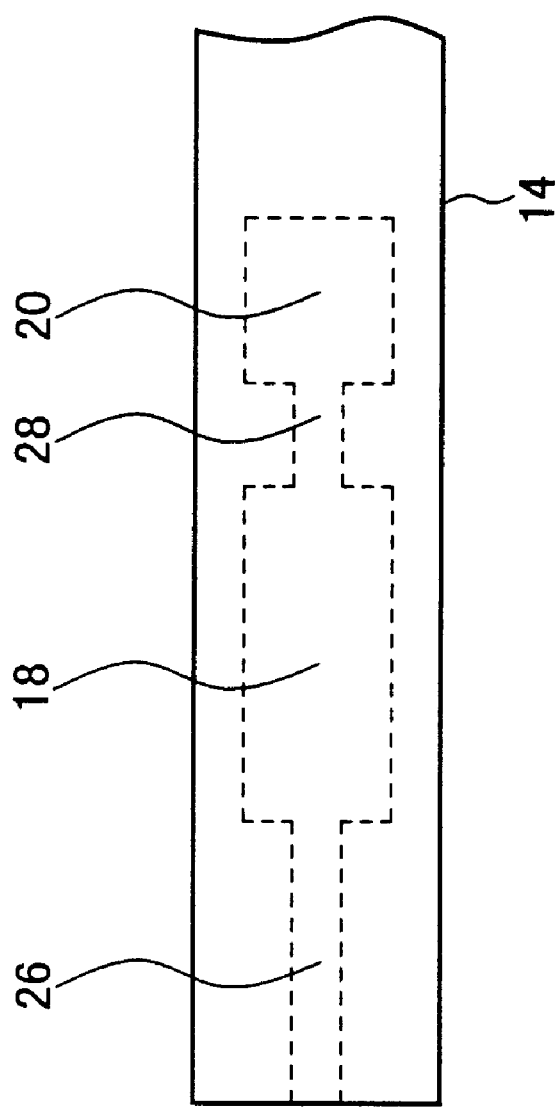
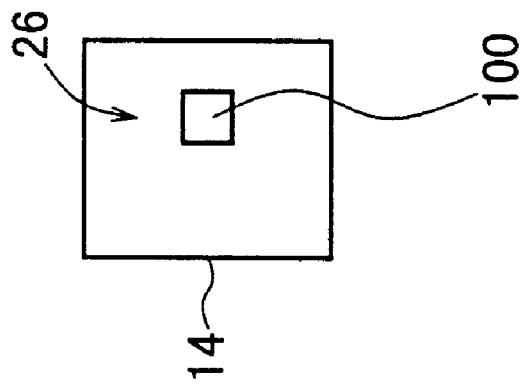

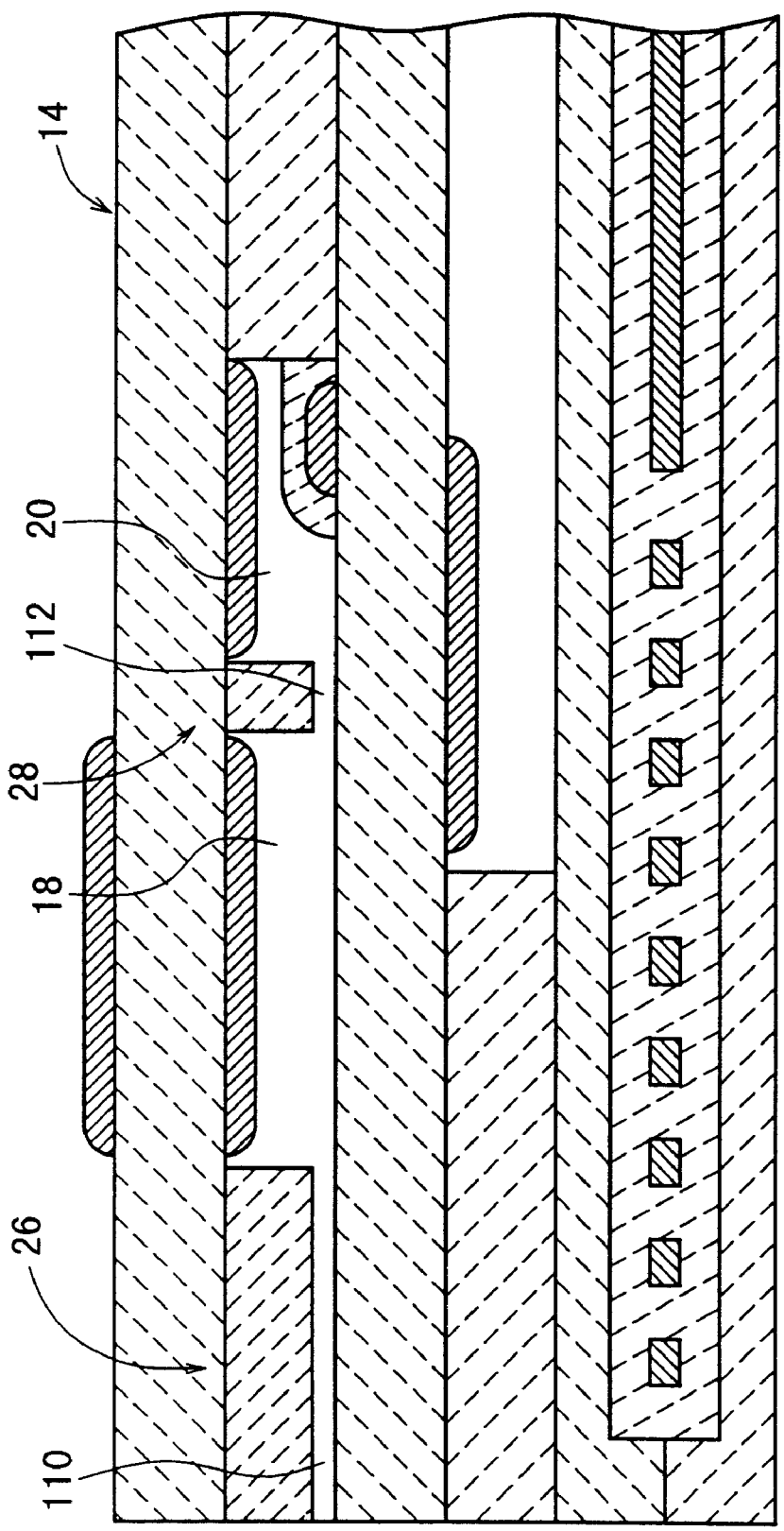

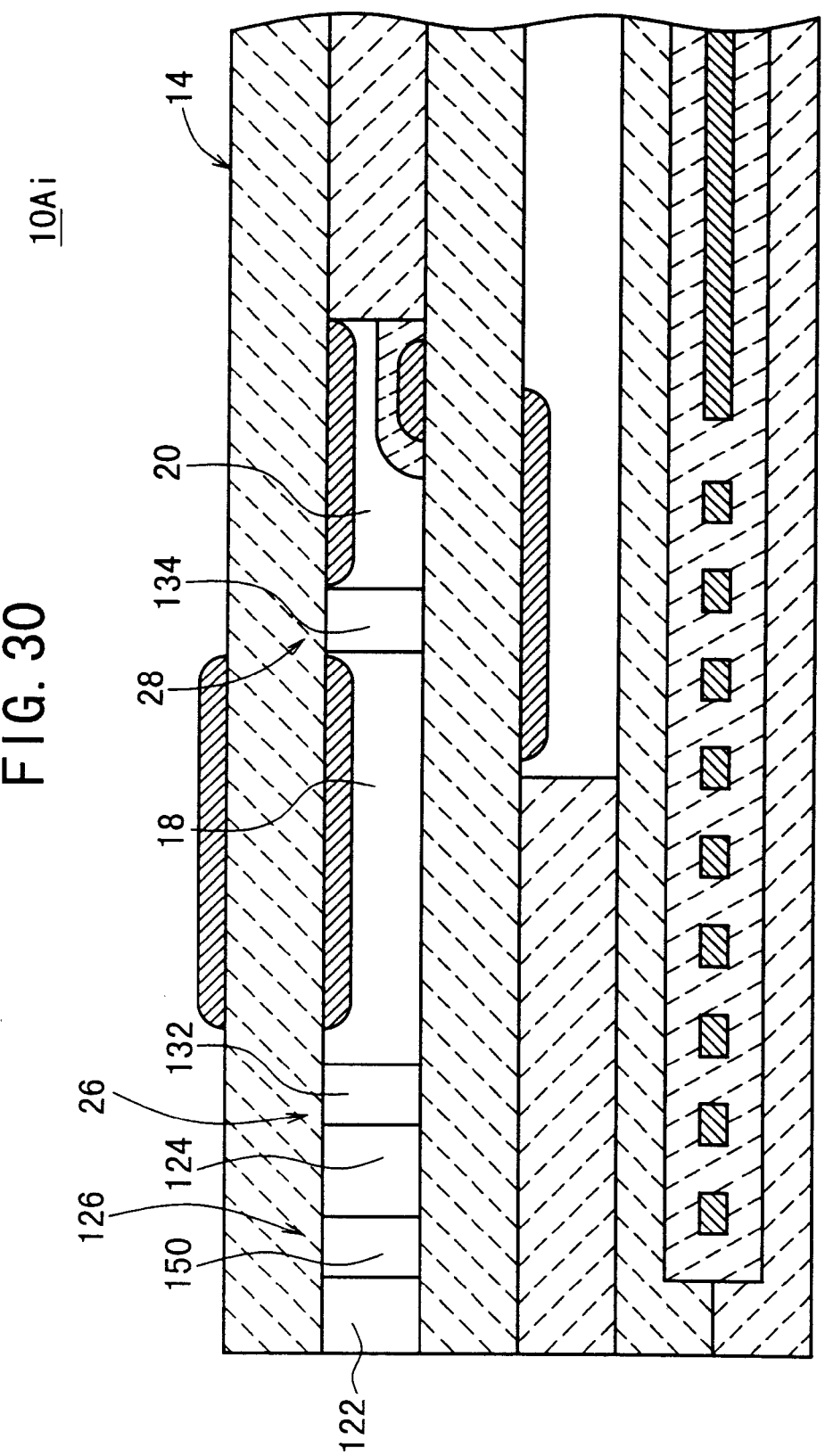

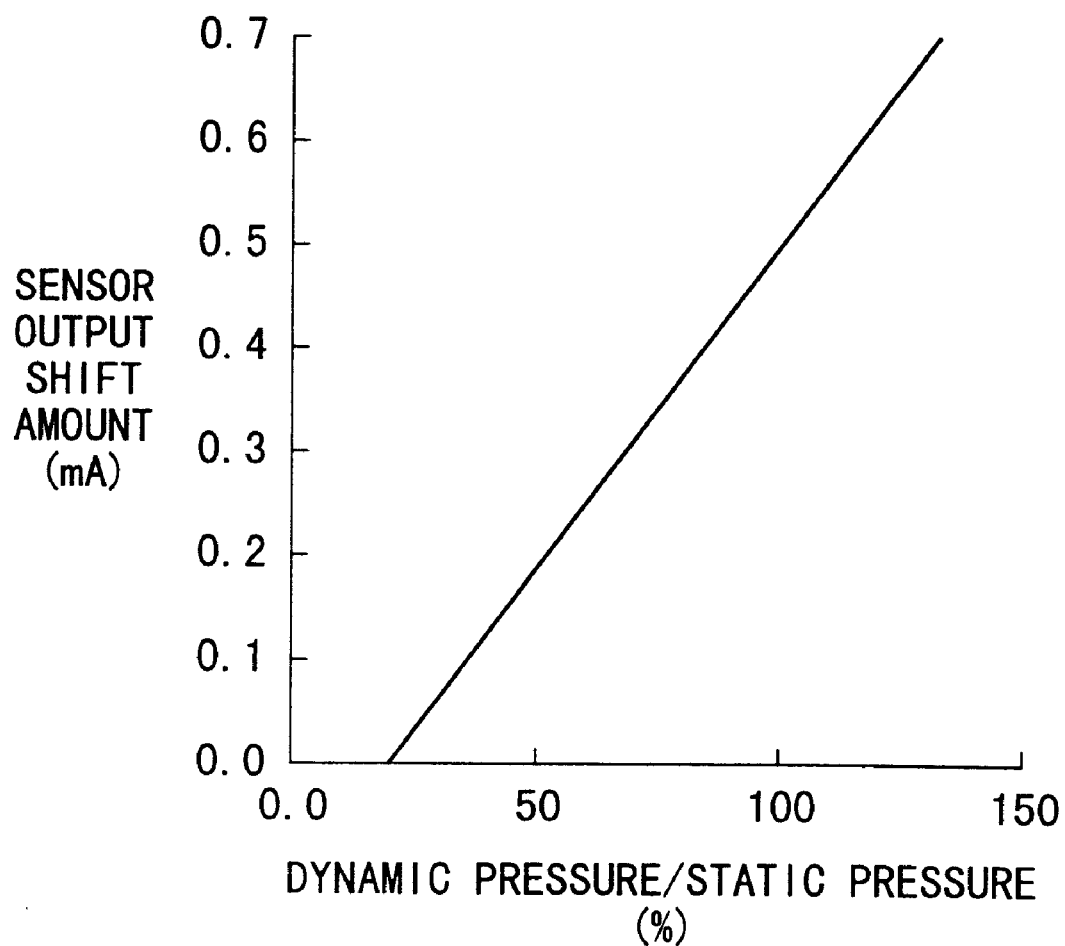

GAS SENSOR AND NITROGEN OXIDE SENSOR

BACKGROUND OF THE INVENTION

1. Field of the Invention

The present invention relates to a gas sensor and a nitrogen oxide sensor for measuring oxides such as $O_2$, NO, $NO_2$, $SO_2$, $CO_2$, and $H_2O$ contained in, for example, atmospheric air and exhaust gas discharged from vehicles or automobiles, and inflammable gases such as CO and CnHm.

2. Description of the Related Art

Those hitherto known as the method for measuring NOx in a measurement gas such as combustion gas include a technique in which the NOx-reducing ability of Rh is utilized to use a sensor comprising a Pt electrode and an Rh electrode formed on an oxygen ion-conductive solid electrolyte such as zirconia so that an electromotive force generated between the both electrodes is measured.

However, the sensor as described above suffers the following problems. That is, the electromotive force is greatly changed depending on the change in concentration of oxygen contained in the combustion gas as the measurement gas. Moreover, the change in electromotive force is small with respect to the change in concentration of NOx. For this reason, the conventional sensor tends to suffer influence of noise.

Further, in order to bring out the NOx-reducing ability, it is indispensable to use a reducing gas such as CO. For this reason, the amount of produced CO is generally smaller than the amount of produced NOx under a lean fuel combustion condition in which a large amount of NOx is produced. Therefore, the conventional sensor has a drawback in that it is impossible to perform the measurement for a combustion gas produced under such a combustion condition.

In order to solve the problems as described above, for example, Japanese Laid-Open Patent Publication No. 8-271476 discloses a NOx sensor comprising pumping electrodes having different NOx-decomposing abilities arranged in a first internal space which communicates with a measurement gas-existing space and in a second internal space which communicates with the first internal space, and a method for measuring the NOx concentration in which the $O_2$ concentration is adjusted by using a first pumping cell arranged in the first internal space, and NO is decomposed by using a decomposing pump arranged in the second internal space so that the NOx concentration is measured on the basis of a pumping current flowing through the decomposing pump.

Further, Japanese Laid-Open Patent Publication No. 9-113484 discloses a sensor element comprising an auxiliary pumping electrode arranged in a second internal space so that the oxygen concentration in the second internal space is controlled to be constant even when the oxygen concentration is suddenly changed.

The following fact has been revealed when a gas sensor is attached to an exhaust system of an internal combustion engine such as an automobile engine, and the internal combustion engine is operated. That is, in ordinary cases, the sensor output ordinarily makes proportional change based on an anchoring point of zero in accordance with the change in oxygen concentration as shown by a solid line "a" in FIG. 32. However, under a specified operation condition, the sensor output is subjected to shift-up as a whole as shown by a solid line "b".

In general, as shown in FIG. 33, the total pressure of the exhaust gas discharged from the automobile engine is composed of a constant static pressure and a dynamic pressure generated by the pulsation of the exhaust gas pressure. The fluctuation cycle of the dynamic pressure is synchronized with the explosion cycle of the engine. As a result of investigation on the cause of the shift-up of the sensor output, it has been revealed that the shift-up occurs when the pulsation amount (=dynamic pressure) of the exhaust gas pressure is large as compared with the static pressure.

That is, as shown in FIG. 34, the shift amount of the sensor output has been measured with respect to the ratio between the dynamic pressure and the static pressure (dynamic pressure/static pressure). As a result, the shift amount is approximately zero when the dynamic pressure/static pressure is not more than about 25%. However, the shift amount increases proportionally from the stage at which the dynamic pressure/static pressure exceeds about 25%.

Therefore, when the dynamic pressure is increased, it is inevitable to suffer any deterioration of the correlation between the oxygen-pumping amount effected by the main pump in the first space and the oxygen concentration in the measurement gas. It is feared that the disturbance of the oxygen concentration caused in the first space may bring about any deterioration concerning the control of the oxygen concentration in the second space communicating with the first space and the accuracy of measurement effected by the detecting electrode as the NOx-detecting section.

SUMMARY OF THE INVENTION

The present invention has been made taking such problems into consideration, an object of which is to provide a gas sensor and a nitrogen oxide sensor which make it possible to avoid the influence of the pulsation of the exhaust gas pressure generated in the measurement gas, and improve the measurement accuracy obtained on the detecting electrode.

According to the present invention, there is provided a gas sensor for measuring an amount of a measurement gas component contained in a measurement gas existing in external space; the gas sensor at least comprising a substrate composed of a solid electrolyte to make contact with the external space; an internal space formed at the inside of the substrate; a diffusion rate-determining means formed with a slit for introducing the measurement gas from the external space via a gas-introducing port under a predetermined diffusion resistance; and a pumping means including an inner pumping electrode and an outer pumping electrode formed at the inside and outside of the internal space respectively, for pumping-processing oxygen contained in the measurement gas introduced from the external space, on the basis of a control voltage applied between the electrodes; wherein a dimension of a certain factor for forming a cross-sectional configuration of the diffusion rate-determining means is not more than 10 $\mu$m.

The limiting current value Ip in the pumping means is approximated by the following theoretical expression for the limiting current.

$$Ip \approx (4F/RT) \times D \times (S/L) \times (POe-POd)$$

In the expression, F represents the Faraday constant (=96500 A/sec), R represents the gas constant (=82.05 $cm^3 \cdot atm/mol \cdot K$), T represents the absolute temperature (K), D represents the diffusion coefficient ($cm^2$/sec), S represents the cross-sectional area ($cm^2$) of the diffusion rate-determining means, L represents the passage length (cm) of the diffusion rate-determining means, POe represents the partial pressure of oxygen (atm) at the outside of the diffusion rate-determining means, and POd represents the partial pressure of oxygen (atm) at the inside of the diffusion rate-determining means.

The present invention defines the factor for forming the cross-sectional area S of the diffusion rate-determining means in the theoretical limiting current expression. Especially, it is defined that the certain factor of the dimension for forming the cross-sectional area S is not more than 10 $\mu$m.

In this arrangement, the pulsation (=dynamic pressure) of the exhaust gas pressure is attenuated by the wall resistance of the diffusion rate-determining means.

Specifically, the attenuation is effected up to the level at which the ratio between the dynamic pressure and the static pressure (dynamic pressure/static pressure) is not more than 25%. Therefore, it is possible to effectively suppress the shift-up phenomenon of the sensor output which would be otherwise caused by the fluctuation of the dynamic pressure.

It is also preferable for the gas sensor constructed as described above that when the cross-sectional configuration of the diffusion rate-determining means is formed with at least one lateral type slit, the certain factor is a length of the slit in a vertical direction. Alternatively, it is also preferable that when the cross-sectional configuration of the diffusion rate-determining means is formed with at least one vertical type slit, the certain factor is a length of the slit in a lateral direction.

It is also preferable for the gas sensor constructed as described above that a buffering space is provided between the gas-introducing port and the diffusion rate-determining means. Usually, the oxygen suddenly enters the sensor element via the gas-introducing port due to the pulsation of the exhaust gas pressure brought about in the external space. However, in this arrangement, the oxygen from the external space does not enter the processing space directly, but it enters the buffering space disposed at the upstream stage thereof. In other words, the sudden change in oxygen concentration, which is caused by the pulsation of the exhaust gas pressure, is counteracted by the buffering space. Thus, the influence of the pulsation of the exhaust gas pressure, which is exerted on the internal space, is in an almost negligible degree.

As a result, the correlation is improved between the oxygen-pumping amount effected by the pumping means in the processing space and the oxygen concentration in the measurement gas. It is possible to improve the measurement accuracy obtained on the measuring pumping means or the concentration-detecting means. Simultaneously, for example, it is possible to concurrently use the internal space as a sensor for determining the air-fuel ratio.

It is also preferable for the gas sensor constructed as described above that a clogging-preventive section and the buffering space are provided in series between the gas-introducing port and the internal space (processing space); a front aperture of the clogging-preventive section is used to form the gas-introducing port; and a diffusion rate-determining section for giving a predetermined diffusion resistance to the measurement gas is provided between the clogging-preventive section and the buffering space.

In this arrangement, the gas sensor is prevented from clogging of particles (for example, soot and oil combustion waste) produced in the measurement gas in the external space, which would be otherwise caused in the vicinity of the inlet of the buffering space. Thus, it is possible to measure the predetermined gas component more accurately. Further, it is possible to maintain a highly accurate state over a long period of time.

It is also preferable for the gas sensor constructed as described above that the oxygen contained in the measurement gas introduced from the external space into the internal space is pumping-processed by using the pumping means to make control so that a partial pressure of oxygen in the internal space (processing space) has a predetermined value at which a predetermined gas component in the measurement gas is not decomposable.

It is also preferable that the gas sensor further comprises a measuring pumping means for decomposing the predetermined gas component contained in the measurement gas after being pumping-processed by the pumping means, by means of catalytic action and/or electrolysis, and pumping processing oxygen produced by the decomposition; wherein the predetermined gas component contained in the measurement gas is measured on the basis of a pumping current flowing through the measuring pumping means in accordance with the pumping process effected by the measuring pumping means.

Alternatively, it is also preferable that the gas sensor further comprises an oxygen partial pressure-detecting means for decomposing the predetermined gas component contained in the measurement gas after being pumping-processed by the pumping means, by means of catalytic action, and generating an electromotive force corresponding to a difference between an amount of oxygen produced by the decomposition and an amount of oxygen contained in a reference gas; wherein the predetermined gas component contained in the measurement gas is measured on the basis of the electromotive force detected by the oxygen partial pressure-detecting means.

According to another aspect of the present invention, there is provided a nitrogen oxide sensor for measuring an amount of a nitrogen oxide component contained in a measurement gas existing in external space; the nitrogen oxide sensor at least comprising a substrate composed of an oxygen ion-conductive solid electrolyte to make contact with the external space; a first internal space formed at the inside of the substrate and communicating with the external space; a first diffusion rate-determining means formed with a slit for introducing the measurement gas into the first internal space under a predetermined diffusion resistance; a main pumping means including a first inner pumping electrode and a first outer pumping electrode formed at the inside and outside of the first internal space respectively, for pumping-processing oxygen contained in the measurement gas introduced from the external space, on the basis of a control voltage applied between the electrodes so that a partial pressure of oxygen in the first internal space is controlled to have a predetermined value at which NO is not substantially decomposable; a second internal space communicating with the first internal space; a second diffusion rate-determining means formed with a slit for introducing an atmosphere pumping-processed in the first internal space into the second internal space under a predetermined diffusion resistance; and a measuring pumping means including a second inner pumping electrode and a second outer pumping electrode formed at the inside and outside of the second internal space respectively, for decomposing NO contained in the atmosphere introduced from the first internal space, by means of catalytic action and/or electrolysis to pumping-process oxygen produced by the decomposition; wherein the amount of nitrogen oxide contained in the measurement gas is measured on the basis of a pumping current flowing through the measuring pumping means in accordance with the pumping process effected by the measuring pumping means; and a dimension of a certain factor for forming a cross-sectional configuration of at least one of the diffusion rate-determining means is not more than 10 µm According to the present invention, the pulsation (=dynamic pressure) of the exhaust gas pressure is attenuated by the wall resistance of the diffusion rate-determining means. Specifically, the attenuation is effected up to the level at which the ratio between the dynamic pressure and the static pressure (dynamic pressure/static pressure) is not more than 25%. Therefore, it is possible to effectively suppress the shift-up phenomenon of the sensor output which would be otherwise caused by the fluctuation of the dynamic pressure.

According to still another aspect of the present invention, there is provided a nitrogen oxide sensor for measuring an amount of a nitrogen oxide component contained in a measurement gas existing in external space; the nitrogen oxide sensor at least comprising a substrate composed of an oxygen ion-conductive solid electrolyte to make contact with the external space: a first internal space formed at the inside of the substrate and communicating with the external space; a first diffusion rate-determining means formed with a slit for introducing the measurement gas into the first internal space under a predetermined diffusion resistance; a main pumping means including an inner pumping electrode and an outer pumping electrode formed at the inside and outside of the first internal space respectively, for pumping-processing oxygen contained in the measurement gas introduced from the external space, on the basis of a control voltage applied between the electrodes so that a partial pressure of oxygen in the first internal space is controlled to have a predetermined value at which NO is not substantially decomposable; a second internal space communicating with the first internal space; a second diffusion rate-determining means formed with a slit for introducing an atmosphere pumping-processed in the first internal space into the second internal space under a predetermined diffusion resistance; and an oxygen partial pressure-detecting means including an inner measuring electrode and an outer measuring electrode formed at the inside and outside of the second internal space respectively, for decomposing NO contained in the atmosphere introduced from the first internal space, by means of catalytic action to generate an electromotive force corresponding to a difference between an amount of oxygen produced by the decomposition and an amount of oxygen contained in a reference gas; wherein the amount of nitrogen oxide contained in the measurement gas is measured on the basis of the electromotive force detected by the oxygen partial pressure-detecting means; and a dimension of a certain factor for forming a cross-sectional configuration of at least one of the diffusion rate-determining means is not more than 10 µm.

Also in this aspect, the pulsation (=dynamic pressure) of the exhaust gas pressure is attenuated by the wall resistance of the diffusion rate-determining means. Specifically, the attenuation is effected up to the level at which the ratio between the dynamic pressure and the static pressure (dynamic pressure/static pressure) is not more than 25%. Therefore, it is possible to effectively suppress the shift-up phenomenon of the sensor output which would be otherwise caused by the fluctuation of the dynamic pressure.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 3A shows a front view illustrating an arrangement concerning Working Example used in first and second illustrative experiments;

FIG. 3B shows a plan view thereof;

FIG. 5A shows a front view illustrating an arrangement concerning Comparative Example used in the first and second illustrative experiments;

FIG. 5B shows a plan view thereof;

FIG. 14 shows a sectional view taken along a line XIV—XIV shown in FIG. 13B;

FIG. 30 shows a sectional view taken along a line XXX—XXX shown in FIG. 29B;

FIG. 34 shows the characteristic illustrating the shift amount of the sensor output with respect to the ratio between the dynamic pressure and the static pressure (dynamic pressure/static pressure).

DESCRIPTION OF THE PREFERRED EMBODIMENTS

Explanation will be made below with reference to FIGS. 1A to 31 for several illustrative embodiments in which the gas sensor according to the present invention is applied to gas sensors for measuring oxides such as $O_2$, NO, $NO_2$, $SO_2$, $CO_2$, and $H_2O$ contained in, for example, atmospheric air and exhaust gas discharged from vehicles or automobiles, and inflammable gases such as CO and CnHm.

Figure 1B:
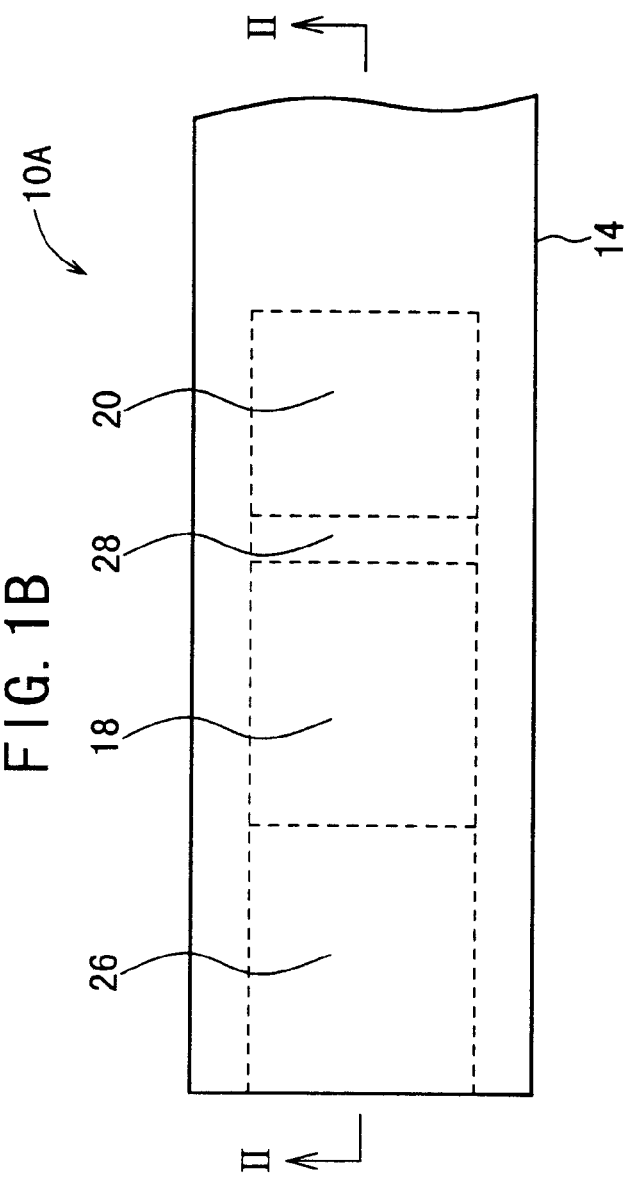
FIG. 1B shows a plan view thereof.
Figure 1A:
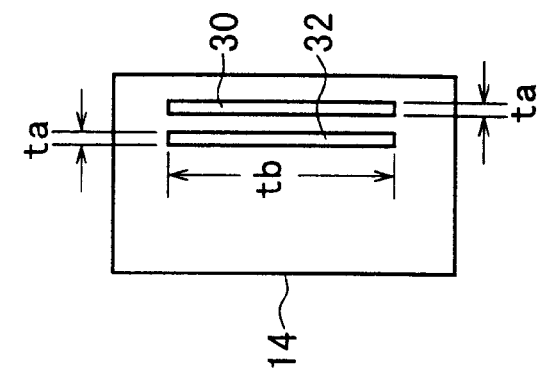
FIG. 1A shows a front view illustrating an arrangement of a gas sensor according to a first embodiment.
Figure 2:
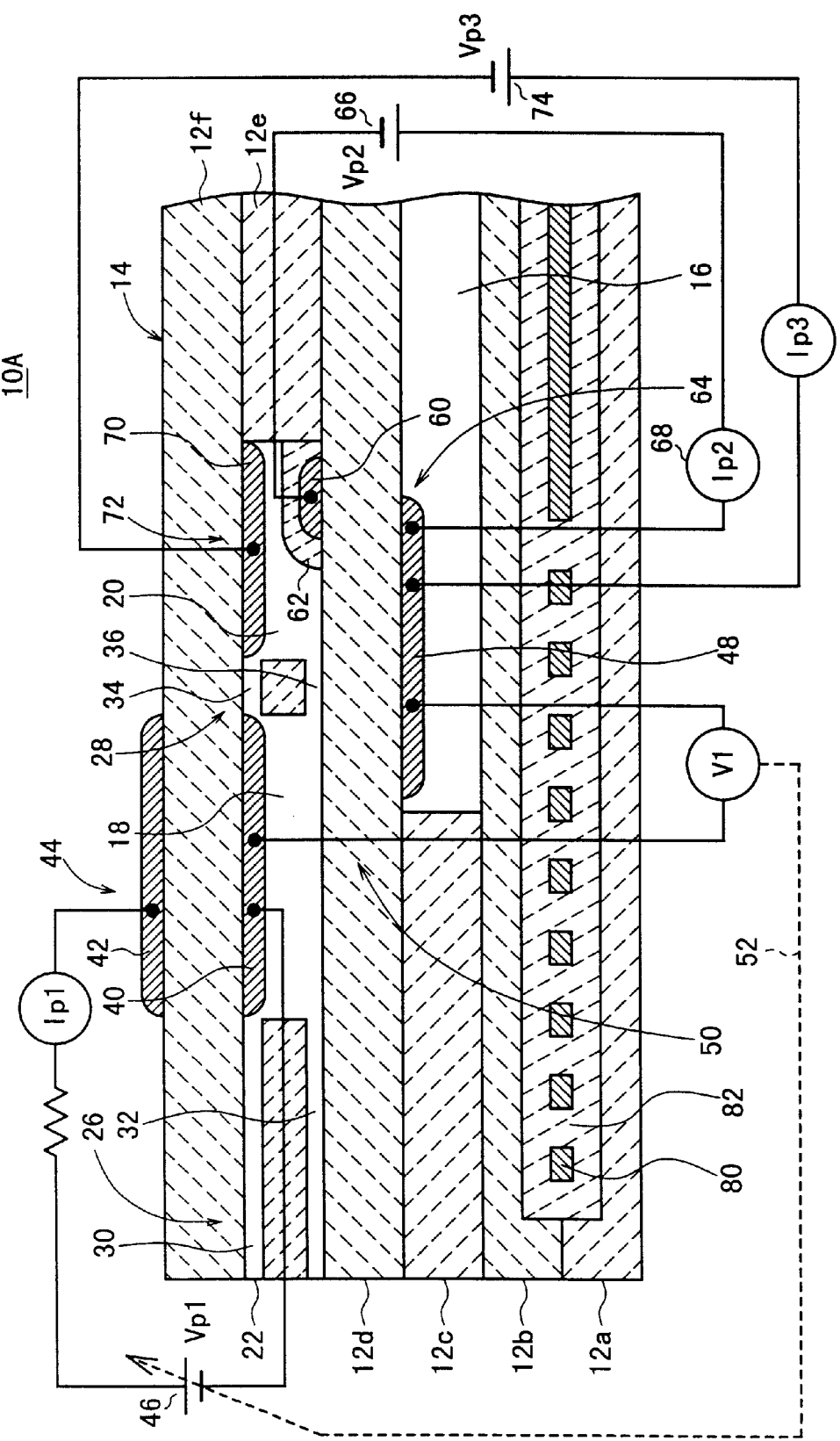
FIG. 2 shows a sectional view taken along a line II—II shown in FIG. 1B.

As shown in FIGS. 1A, 1B, and 2, a gas sensor 10A according to the first embodiment includes a sensor element 14 provided with a substrate comprising, for example, six stacked solid electrolyte layers 12a to 12f composed of ceramics based on the use of oxygen ion-conductive solid electrolytes such as $ZrO_2$.

In the sensor element 14, first and second layers from the bottom are designated as first and second substrate layers 12a, 12b respectively. Third and fifth layers from the bottom are designated as first and second spacer layers 12c, 12e respectively. Fourth and sixth layers from the bottom are designated as first and second solid electrolyte layers 12d, 12f respectively.

A space 16 (reference gas-introducing space 16), into which a reference gas such as atmospheric air to be used as a reference for measuring oxides is introduced, is formed between the second substrate layer 12b and the first solid electrolyte layer 12d, the space 16 being comparted by a lower surface of the first solid electrolyte layer 12d, an upper surface of the second substrate layer 12b, and side surfaces of the first spacer layer 12c.

A first chamber 18 for adjusting the partial pressure of oxygen in a measurement gas is formed and comparted between a lower surface of the second solid electrolyte layer 12f and an upper surface of the first solid electrolyte layer 12d. A second chamber 20 for finely adjusting the partial pressure of oxygen in the measurement gas and measuring oxides, for example, nitrogen oxides (NOx) in the measurement gas is formed and comparted between the lower surface of the second solid electrolyte layer 12f and the upper surface of the first solid electrolyte layer 12d.

A gas-introducing port 22, which is formed at the forward end of the sensor element 14, communicates with the first chamber 18 via a first diffusion rate-determining section 26. The first chamber 18 communicates with the second chamber 20 via a second diffusion rate-determining section 28.

In this embodiment, each of the first and second diffusion rate-determining sections 26, 28 gives a predetermined diffusion resistance to the measurement gas to be introduced into the first chamber 18 and the second chamber 20 respectively. As shown in FIG. 1A, the first diffusion rate-determining section 26 is formed by two laterally extending slits 30, 32. Specifically, the first diffusion rate-determining section 26 includes the slit 30 having a laterally extending aperture formed at a front end portion of the second spacer layer 12e to make contact with the lower surface of the second solid electrolyte layer 12f, the aperture being formed to extend with an identical aperture width up to the first chamber 18. The first diffusion rate-determining section 26 also includes the slit 32 having a laterally extending aperture formed at a front end portion of the second spacer layer 12e to make contact with the upper surface of the first solid electrolyte layer 12d, the aperture being formed to extend with an identical aperture width up to the first chamber 18.

In the first embodiment, the respective slits 30, 32 have approximately the same cross-sectional configuration. As shown in FIG. 1A, the length ta in the vertical direction is not more than 10 $\mu$m. and the length tb in the lateral direction is about 2 mm.

The second diffusion rate-determining section 28 is also formed with two laterally extending slits 34, 36 each having a cross-sectional configuration similar to those of the first diffusion rate-determining section 26. It is allowable that a porous member composed of $ZrO_2$ or the like is arranged and packed in each of the slits 34, 36 of the second diffusion rate-determining section 28 so that the diffusion resistance of the second diffusion rate-determining section 28 is larger than the diffusion resistance of the first diffusion rate-determining section 26. It is preferable that the diffusion resistance of the second diffusion rate-determining section 28 is larger than that of the first diffusion rate-determining section 26. However, no problem occurs even when the former is smaller than the latter.

The atmosphere in the first chamber 18 is introduced into the second chamber 20 under the predetermined diffusion resistance via the second diffusion rate-determining section 28.

An inner pumping electrode 40 having a substantially rectangular planar configuration and composed of a porous cermet electrode (for example, a cermet electrode of Pt·ZrO$_2$ containing 1% Au) is formed on the entire lower surface portion for forming the first chamber 18, of the lower surface of the second solid electrolyte layer 12f. An outer pumping electrode 42 is formed on a portion corresponding to the inner pumping electrode 40, of the upper surface of the second solid electrolyte layer 12f. An electrochemical pumping cell, i.e., a main pumping cell 44 is constructed by the inner pumping electrode 40, the outer pumping electrode 42, and the second solid electrolyte layer 12f interposed between the both electrodes 40, 42.

A desired control voltage (pumping voltage) Vp1 is applied between the inner pumping electrode 40 and the outer pumping electrode 42 of the main pumping cell 44 by the aid of an external variable power source 46 to allow a pumping current Ip1 to flow in a positive or negative direction between the outer pumping electrode 42 and the inner pumping electrode 40. Thus, the oxygen in the atmosphere in the first chamber 18 can be pumped out to the external space, or the oxygen in the external space can be pumped into the first chamber 18.

A reference electrode 48 is formed on a lower surface portion exposed to the reference gas-introducing space 16, of the lower surface of the first solid electrolyte layer 12d. An electrochemical sensor cell, i.e., a controlling oxygen partial pressure-detecting cell 50 is constructed by the inner pumping electrode 40, the reference electrode 48, the second solid electrolyte layer 12f, the second spacer layer 12e, and the first solid electrolyte layer 12d.

The controlling oxygen partial pressure-detecting cell 50 is operated as follows. That is, an electromotive force V1 is generated between the inner pumping electrode 40 and the reference electrode 48 on the basis of a difference in oxygen concentration between the atmosphere in the first chamber 18 and the reference gas (atmospheric air) in the reference gas-introducing space 16. The partial pressure of oxygen in the atmosphere in the first chamber 18 can be detected by using the electromotive force V1.

The detected value of the partial pressure of oxygen is used to feedback-control the variable power source 46. Specifically, the pumping operation effected by the main pumping cell 44 is controlled by the aid of a feedback control system 52 for the main pump so that the partial pressure of oxygen in the atmosphere in the first chamber 18 has a predetermined value which is sufficiently low to control the partial pressure of oxygen in the second chamber 20 in the next step.

The feedback control system 52 comprises a circuit constructed to feedback-control the pumping current Vp1 between the outer pumping electrode 42 and the inner pumping electrode 40 so that a difference (detection voltage V1) between an electric potential of the inner pumping electrode 40 and an electric potential of the reference electrode 48 is at a predetermined voltage level. In this embodiment, the inner pumping electrode 40 is grounded.

Therefore, the main pumping cell 44 pumps out or pumps in oxygen in an amount corresponding to the level of the pumping voltage Vp1, of the measurement gas introduced into the first chamber 18. The oxygen concentration in the first chamber 18 is subjected to feedback control to give a predetermined level by repeating the series of operations described above. In this state, the pumping current Ip1, which flows between the outer pumping electrode 42 and the inner pumping electrode 40, indicates the difference between the oxygen concentration in the measurement gas and the controlled oxygen concentration in the first chamber 18. The pumping current Ip1 can be used to measure the oxygen concentration in the measurement gas.

Each of the inner pumping electrode 40 and the outer pumping electrode 42 is composed of a porous cermet electrode which is made of a metal such as Pt and ceramics such as ZrO$_2$. It is necessary to use a material which has a weak reducing ability or no reducing ability with respect to the NO component in the measurement gas, for the inner pumping electrode 40 disposed in the first chamber 18 to make contact with the measurement gas. It is preferable that the inner pumping electrode 40 is composed of, for example, a compound having the perovskite structure such as La$_3$CuO$_4$, a cermet comprising ceramics and a metal such as Au having a low catalytic activity, or a cermet comprising ceramics, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

In the gas sensor 10A according to the first embodiment, a detecting electrode 60 having a substantially rectangular planar configuration and composed of a porous cermet electrode is formed at a portion separated from the second diffusion rate-determining section 28, on an upper surface portion for forming the second chamber 20, of the upper surface of the first solid electrolyte layer 12d. An alumina film for constructing a third diffusion rate-determining section 62 is formed so that the detecting electrode 60 is covered therewith. An electrochemical pumping cell, i.e., a measuring pumping cell 64 is constructed by the detecting electrode 60, the reference electrode 48, and the first solid electrolyte layer 12d.

The detecting electrode 60 is composed of a porous cermet comprising zirconia as ceramics and a metal capable of reducing NOx as the measurement gas component. Accordingly, the detecting electrode 60 functions as a NOx-reducing catalyst for reducing NOx existing in the atmosphere in the second chamber 20. Further, the oxygen in the atmosphere in the second chamber 20 can be pumped out to the reference gas-introducing space 16 by applying a constant voltage Vp2 between the detecting electrode 60 and the reference electrode 48 by the aid of a DC power source 66. The pumping current Ip2, which is allowed to flow in accordance with the pumping operation performed by the measuring pumping cell 64, is detected by an ammeter 68.

The constant voltage (DC) power source 66 can apply a voltage of a magnitude to give a limiting current to the pumping for oxygen produced during decomposition in the measuring pumping cell 64 under the inflow of NOx restricted by the third diffusion rate-determining section 62.

On the other hand, an auxiliary pumping electrode 70 having a substantially rectangular planar configuration and composed of a porous cermet electrode (for example, a cermet electrode of Pt·ZrO$_2$ containing 1% Au) is formed on the entire lower surface portion for forming the second chamber 20, of the lower surface of the second solid electrolyte layer 12f. An auxiliary electrochemical pumping cell, i.e., an auxiliary pumping cell 72 is constructed by the auxiliary pumping electrode 70, the second solid electrolyte layer 12f, the second spacer layer 12e, the first solid electrolyte layer 12d, and the reference electrode 48.

The auxiliary pumping electrode 70 is based on the use of a material having a weak reducing ability or no reducing ability with respect to the NO component contained in the measurement gas, in the same manner as in the inner pumping electrode 40 of the main pumping cell 44. In this embodiment, it is preferable that the auxiliary pumping electrode 70 is composed of, for example, a compound having the perovskite structure such as $La_3CuO_4$, a cermet comprising ceramics and a metal having a low catalytic activity such as Au, or a cermet comprising ceramics, a metal of the Pt group, and a metal having a low catalytic activity such as Au. Further, when an alloy comprising Au and a metal of the Pt group is used as an electrode material, it is preferable to add Au in an amount of 0.03 to 35% by volume of the entire metal components.

A desired constant voltage Vp3 is applied between the reference electrode 48 and the auxiliary pumping electrode 70 of the auxiliary pumping cell 72 by the aid of an external DC power source 74. Thus, the oxygen in the atmosphere in the second chamber 20 can be pumped out to the reference gas-introducing space 16.

Accordingly, the partial pressure of oxygen in the atmosphere in the second chamber 20 is allowed to have a low value of partial pressure of oxygen at which the measurement of the amount of the objective component is not substantially affected, under the condition in which the measurement gas component (NOx) is not substantially reduced or decomposed. In this embodiment, owing to the operation of the main pumping cell 44 for the first chamber 18, the change in amount of oxygen introduced into the second chamber 20 is greatly reduced as compared with the change in the measurement gas. Accordingly, the partial pressure of oxygen in the second chamber 20 is accurately controlled to be constant.

Therefore, in the gas sensor 10A according to the first embodiment constructed as described above, the measurement gas, for which the partial pressure of oxygen has been controlled in the second chamber 20, is introduced into the detecting electrode 60.

As shown in FIG. 2, the gas sensor 10A according to the first embodiment further comprises a heater 80 for generating heat in accordance with electric power supply from the outside. The heater 80 is embedded in a form of being vertically interposed between the first and second substrate layers 12a, 12b. The heater 80 is provided in order to increase the conductivity of oxygen ion. An insulative layer 82 composed of alumina or the like is formed to cover upper and lower surfaces of the heater 80 so that the heater 80 is electrically insulated from the first and second substrate layers 12a, 12b.

The heater 80 is arranged over the entire portion ranging from the first chamber 18 to the second chamber 20. Accordingly, each of the first chamber 18 and the second chamber 20 is heated to a predetermined temperature. Simultaneously, each of the main pumping cell 44, the controlling oxygen partial pressure-detecting cell 50, and the measuring pumping cell 64 is also heated to a predetermined temperature and maintained at that temperature.

Next, the operation of the gas sensor 10A according to the first embodiment will be explained. At first, the forward end of the gas sensor 10A is disposed in the external space. Accordingly, the measurement gas is introduced into the first chamber 18 under the predetermined diffusion resistance via the first diffusion rate-determining section 26 (slits 30, 32). The measurement gas, which has been introduced into the first chamber 18, is subjected to the pumping action for oxygen, caused by applying the predetermined pumping voltage Vp1 between the outer pumping electrode 42 and the inner pumping electrode 40 which construct the main pumping cell 44. The partial pressure of oxygen is controlled to have a predetermined value, for example, $10^{-7}$ atm. The control is performed by the aid of the feedback control system 52.

The first diffusion rate-determining section 26 serves to limit the amount of diffusion and inflow of oxygen in the measurement gas into the measuring space (first chamber 18) when the pumping voltage Vp1 is applied to the main pumping cell 44 so that the current flowing through the main pumping cell 44 is suppressed.

In the first chamber 18, a state of partial pressure of oxygen is established, in which NOx in the atmosphere is not reduced by the inner pumping electrode 40 in an environment of being heated by the external measurement gas and being heated by the heater 80. For example, a condition of partial pressure of oxygen is formed, in which the reaction of $NO \rightarrow 1/2N_2 + 1/2O_2$ does not occur, because of the following reason. That is, if NOx in the measurement gas (atmosphere) is reduced in the first chamber 18, it is impossible to accurately measure NOx in the second chamber 20 disposed at the downstream stage. In this context, it is necessary to establish a condition in the first chamber 18 in which NOx is not reduced by the component which participates in reduction of NOx (in this case, the metal component of the inner pumping electrode 40). Specifically, as described above, such a condition is achieved by using, for the inner pumping electrode 40, the material having a low ability to reduce NOx, for example, an alloy of Au and Pt.

The gas in the first chamber 18 is introduced into the second chamber 20 under the predetermined diffusion resistance via the second diffusion rate-determining section 28. The gas, which has been introduced into the second chamber 20, is subjected to the pumping action for oxygen, caused by applying the voltage Vp3 between the reference electrode 48 and the auxiliary pumping electrode 70 which constitute the auxiliary pumping cell 72 to make fine adjustment so that the partial pressure of oxygen has a constant and low value of partial pressure of oxygen.

The second diffusion rate-determining section 28 serves to limit the amount of diffusion and inflow of oxygen in the measurement gas into the measuring space (second chamber 20) when the voltage Vp3 is applied to the auxiliary pumping cell 72 so that the pumping current Ip3 flowing through the auxiliary pumping cell 72 is suppressed, in the same manner as performed by the first diffusion rate-determining section 26.

The measurement gas, which has been controlled for the partial pressure of oxygen in the second chamber 20 as described above, is introduced into the detecting electrode 60 under the predetermined diffusion resistance via the third diffusion rate-determining section 62.

When it is intended to control the partial pressure of oxygen in the atmosphere in the first chamber 18 to have a low value of the partial pressure of oxygen which does not substantially affect the measurement of NOx, by operating the main pumping cell 44, in other words, when the pumping voltage Vp1 of the variable power source 46 is adjusted by the aid of the feedback control system 52 so that the voltage V1 detected by the controlling oxygen partial pressure-detecting cell 50 is constant, if the oxygen concentration in the measurement gas greatly changes, for example, in a range of 0 to 20%, then the respective partial pressures of oxygen in the atmosphere in the second chamber 20 and in the atmosphere in the vicinity of the detecting electrode 60 slightly change in ordinary cases. This phenomenon is caused probably because of the following reason. That is, when the oxygen concentration in the measurement gas increases, the distribution of the oxygen concentration occurs in the widthwise direction and in the thickness direction in the first chamber 18. The distribution of the oxygen concentration changes depending on the oxygen concentration in the measurement gas.

However, in the case of the gas sensor 10A according to the first embodiment, the auxiliary pumping cell 72 is provided for the second chamber 20 so that the partial pressure of oxygen in its internal atmosphere always has a constant low value of the partial pressure of oxygen. Accordingly, even when the partial pressure of oxygen in the atmosphere introduced from the first chamber 18 into the second chamber 20 changes depending on the oxygen concentration in the measurement gas, the partial pressure of oxygen in the atmosphere in the second chamber 20 can be always made to have a constant low value, owing to the pumping action performed by the auxiliary pumping cell 72. As a result, the partial pressure of oxygen can be controlled to have a low value at which the measurement of NOx is not substantially affected.

NOx in the measurement gas introduced into the detecting electrode 60 is reduced or decomposed around the detecting electrode 60. Thus, for example, a reaction of NO→1/2N$_2$+ 1/2O$_2$ is allowed to occur. In this process, a predetermined voltage Vp2, for example, 430 mV (700° C.) is applied between the detecting electrode 60 and the reference electrode 48 which construct the measuring pumping cell 64, in a direction to pump out the oxygen from the second chamber 20 to the reference gas-introducing space 16.

Therefore, the pumping current Ip2 flowing through the measuring pumping cell 64 has a value which is proportional to a sum of the oxygen concentration in the atmosphere introduced into the second chamber 20, i.e., the oxygen concentration in the second chamber 20 and the oxygen concentration produced by reduction or decomposition of NOx by the aid of the detecting electrode 60.

In this embodiment, the oxygen concentration in the atmosphere in the second chamber 20 is controlled to be constant by means of the auxiliary pumping cell 72. Accordingly, the pumping current Ip2 flowing through the pumping cell 64 is proportional to the NOX concentration. The NOx concentration corresponds to the amount of diffusion of NOx limited by the third diffusion rate-determining section 62. Therefore, even when the oxygen concentration in the measurement gas greatly changes, it is possible to accurately measure the NOx concentration, based on the use of the measuring pumping cell 64 by the aid of the ammeter 68.

According to the fact described above, almost all of the pumping current value Ip2 obtained by operating the measuring pumping cell 64 represents the amount brought about by the reduction or decomposition of NOx. Accordingly, the obtained result does not depend on the oxygen concentration in the measurement gas.

In the meantime, in ordinary cases, the shift amount increases proportionally from the stage at which the ratio between the dynamic pressure and the static pressure (dynamic pressure/static pressure) exceeds about 25% (see FIG. 34). However, in the gas sensor 10A according to the first embodiment, the length ta in the vertical direction, which is the certain factor for forming the cross-sectional configuration of the first diffusion rate-determining section 26 (slits 30, 32), is not more than 10 μm.

The limiting current value Ip1 in the main pumping cell 44 is approximated by the following theoretical expression for the limiting current.

$$Ip1 \approx (4F/RT) \times D \times (S/L) \times (POe-POd)$$

the expression, F represents the Faraday constant (=96500 A/sec), R represents the gas constant (=82.05 cm$^3$·atm/ mol·K), T represents the absolute temperature (K), D represents the diffusion coefficient (cm$^2$/sec), S represents the cross-sectional area (cm$^2$) of the first diffusion rate-determining section 26 (slit 30 or 32), L represents the passage length (cm) of the first diffusion rate-determining section 26 (slit 30 or 32), POe represents the partial pressure of oxygen (atm) in the external space, and POd represents the partial pressure of oxygen (atm) in the first chamber 18.

In the gas sensor 10A according to the first embodiment, there is defined the formation factor for the cross-sectional area S of the first diffusion rate-determining section 26 (slit 30 or 32) in the theoretical limiting current expression. Especially, it is defined that the certain factor of the dimension for forming the cross-sectional area S, i.e., the length in the vertical direction in this embodiment is not more than 10 μm.

Accordingly, the pulsation (=dynamic pressure) of the exhaust gas pressure is attenuated by the wall resistance of the first diffusion rate-determining section 26. Specifically, the attenuation is effected up to the level at which the ratio between the dynamic pressure and the static pressure (dynamic pressure/static pressure) is not more than 25%. Therefore, it is possible to effectively suppress the shift-up phenomenon of the sensor output (the pumping current value Ip2 concerning the measuring pumping cell or the value of the pumping current Ip1 flowing through the main pumping cell) which would be otherwise caused by the fluctuation of the dynamic pressure.

Two illustrative experiments (conveniently referred to as "first and second illustrative experiments") will now be described. In the first illustrative experiment, the measurement was made for the way of change of the sensor output obtained when the oxygen concentration in the measurement gas was changed concerning Working Example and Comparative Example. In the second illustrative experiment, the measurement was made for the way of change of the sensor output obtained when the NOx concentration in the measurement gas was changed.

The following measurement condition was adopted. That is, a diesel engine of 2.5 L was used as an engine, the number of revolution was 1000 to 4000 rpm, and the engine load was 5 to 20 kgm. The number of revolution, the engine load, and the EGR opening degree were appropriately changed to measure the fluctuation of the sensor output obtained under the respective conditions as well.

Figure 4:
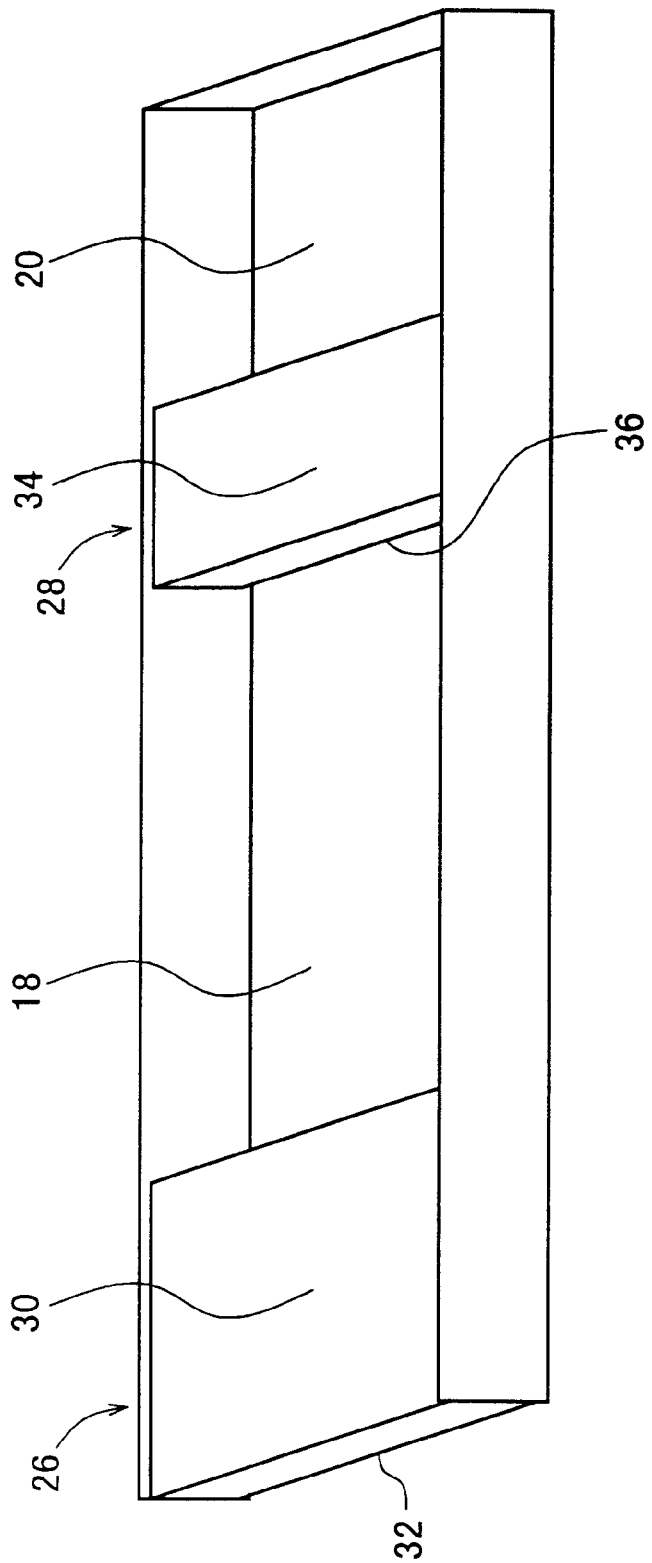
FIG. 4 shows a perspective view illustrating the arrangement concerning Working Example used in the first and second illustrative experiments, especially illustrating extracted arrangements of first and second diffusion rate-determining sections.
Figure 6:
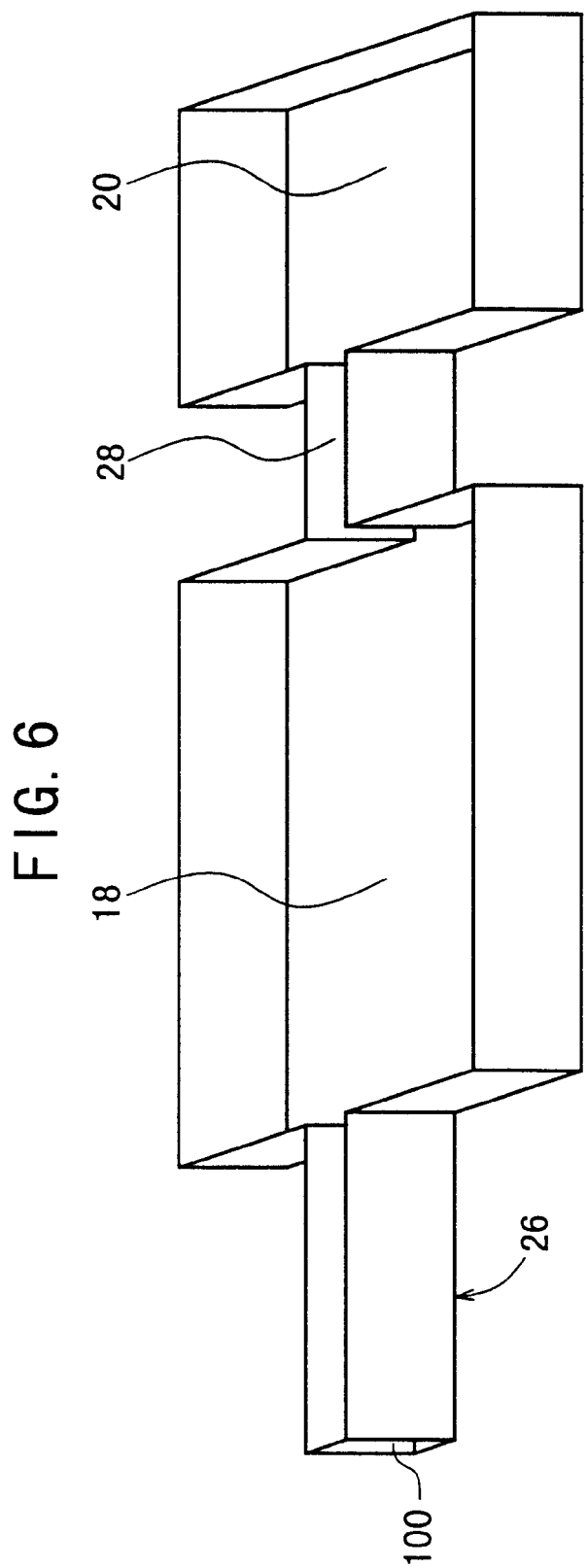
FIG. 6 shows a perspective view illustrating the arrangement concerning Comparative Example used in the first and second illustrative experiments, especially illustrating extracted arrangements of first and second diffusion rate-determining sections.

Working Example is illustrative of the case in which the first diffusion rate-determining section 26 was constructed by upper and lower two laterally extending slits 30, 32 (length in the lateral direction: 2 mm×length in the vertical direction: not more than 10 μm) as shown in FIGS. 3A, 3B, and 4 in the same manner as in the gas sensor 10A according to the first embodiment. Comparative Example is illustrative of the case in which the first diffusion rate-determining section 26 was constructed by a single slit 100 (length in the lateral direction: 0.2 mm×length in the vertical direction: 0.2 mm) as shown in FIGS. 5A, 5B, and 6 concerning the gas sensor 10A according to the first embodiment.

Figure 7:
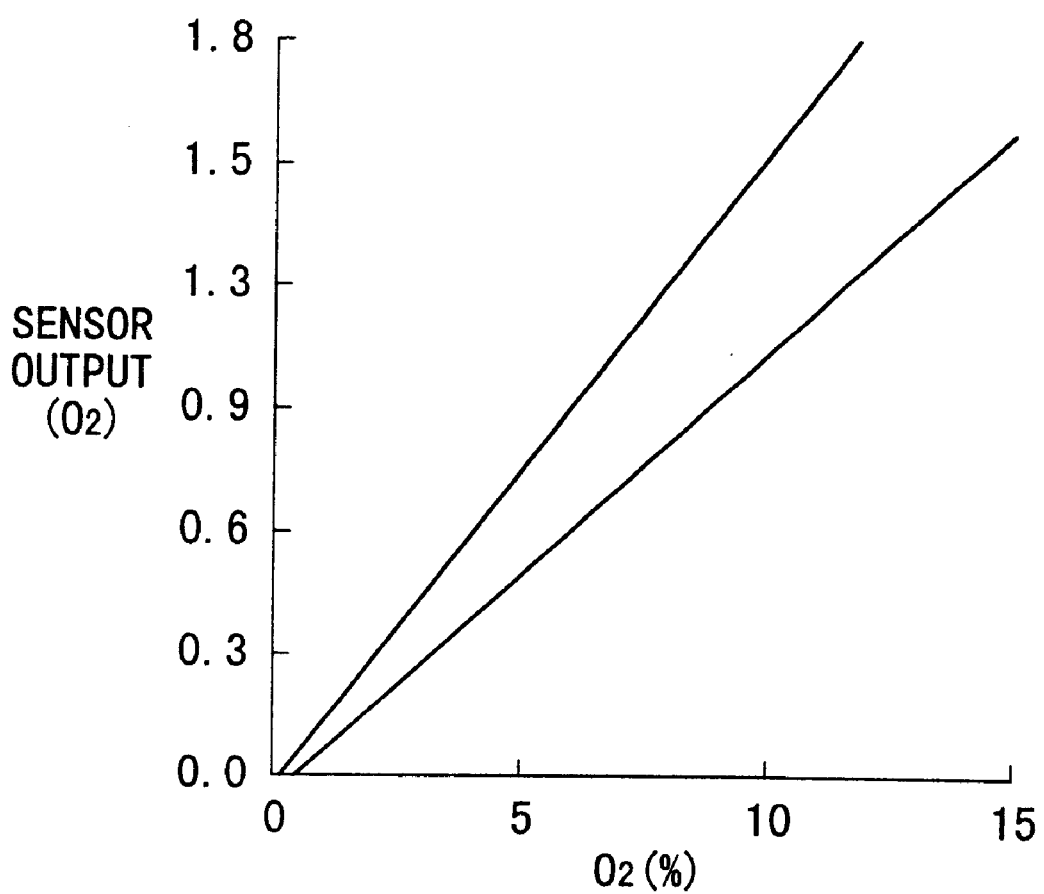
FIG. 7 shows the characteristic illustrating the change in sensor output with respect to the oxygen concentration, obtained when the measurement condition is changed in Comparative Example.
Figure 8:
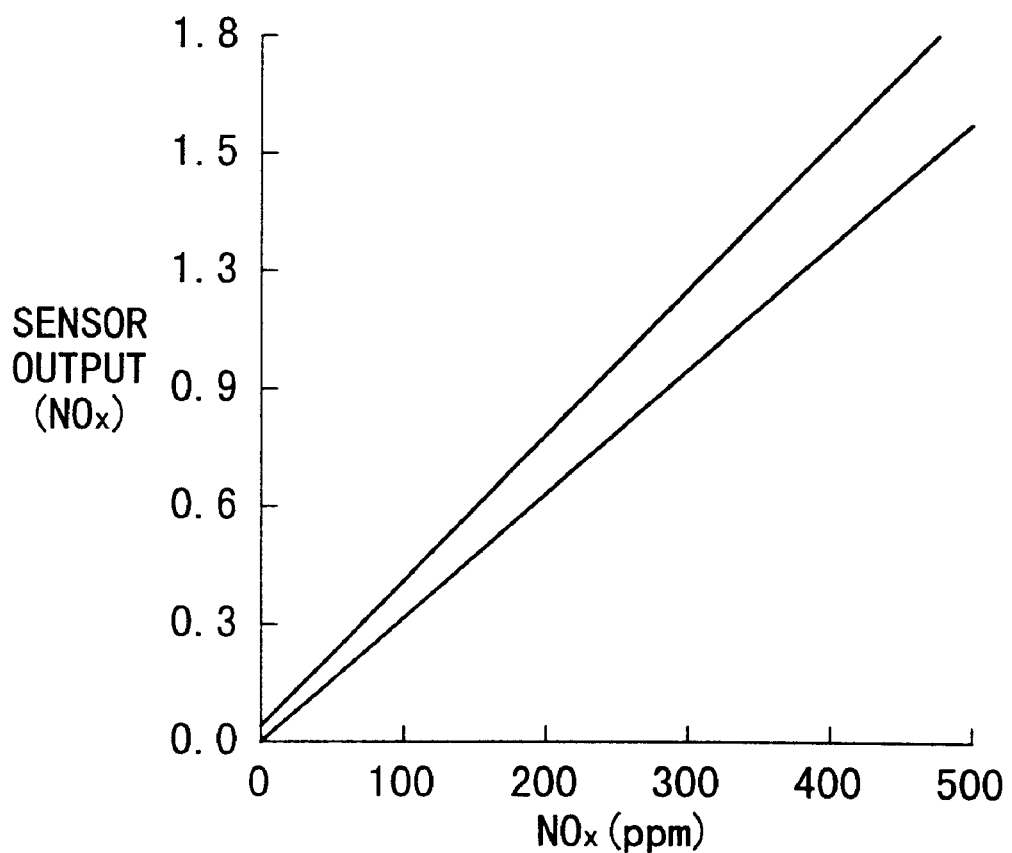
FIG. 8 shows the characteristic illustrating the change in sensor output with respect to the NOx concentration, obtained when the measurement condition is changed in Comparative Example.
Figure 9:
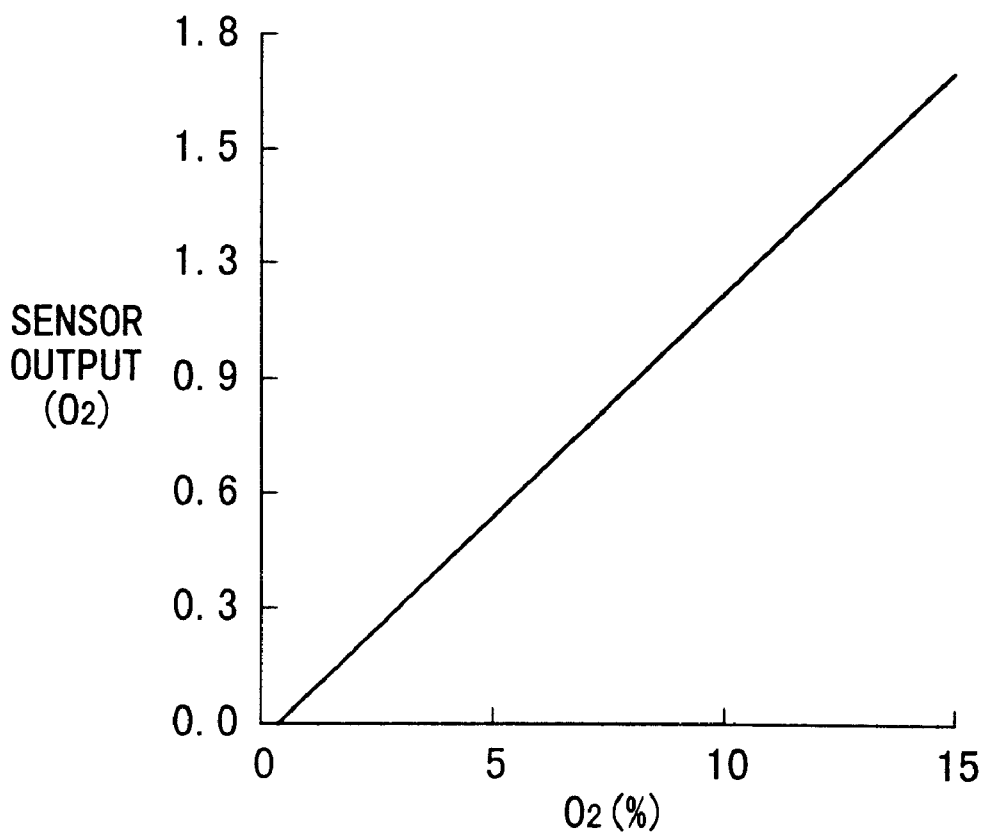
FIG. 9 shows the characteristic illustrating the change in sensor output with respect to the oxygen concentration, obtained when the measurement condition is changed in Working Example.
Figure 10:
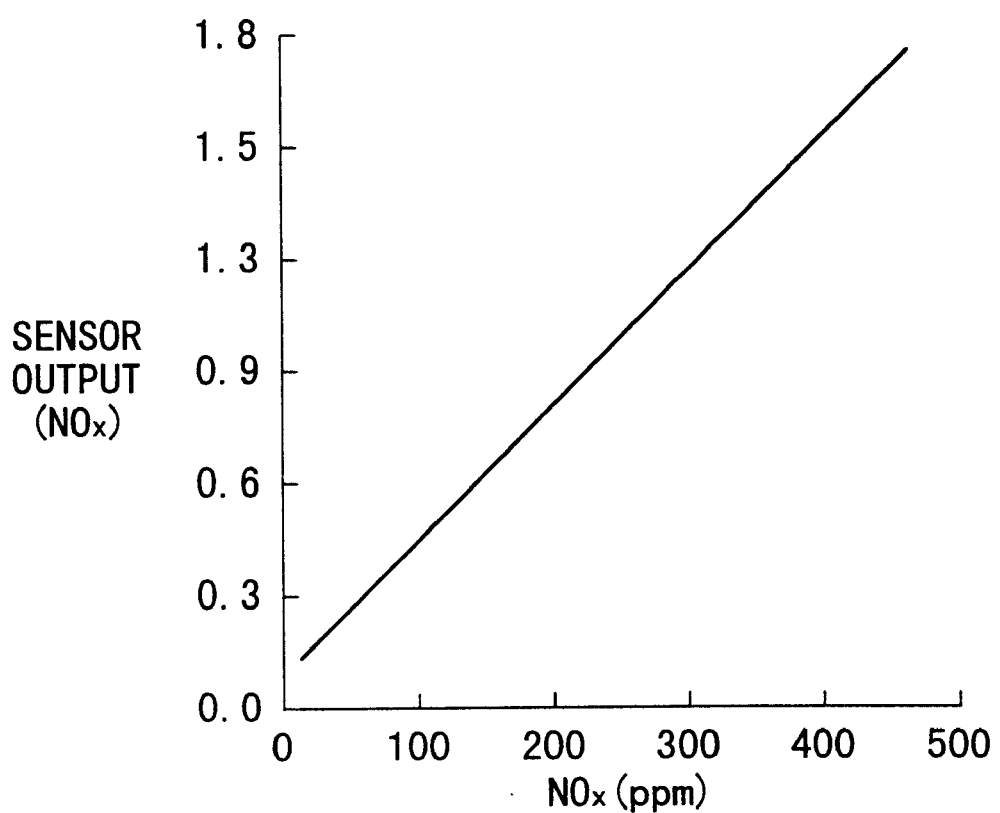
FIG. 10 shows the characteristic illustrating the change in sensor output with respect to the NOx concentration, obtained when the measurement condition is changed in Working Example.

Experimental results obtained in the first and second illustrative experiments are shown in FIGS. 7 and 8 (Comparative Example) and in FIGS. 9 and 10 (Working Example). It is understood that in Comparative Example as shown in FIGS. 7 and 8, the sensor output fluctuates by changing the measurement condition, and the fluctuation of the sensor output is conspicuous especially when the engine load is high.

Figure 11A:
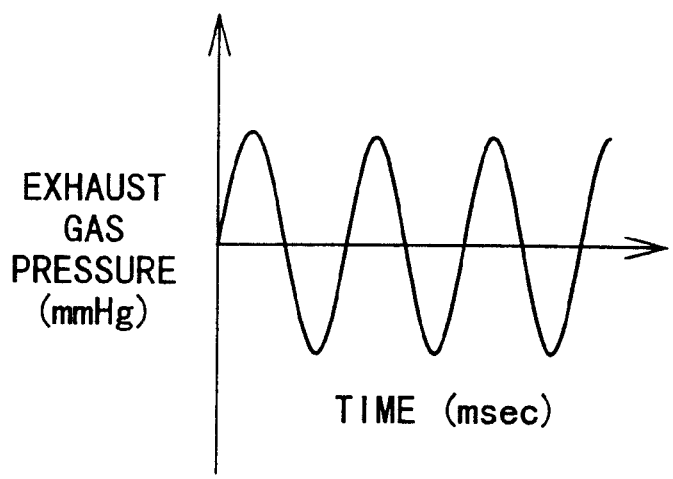
FIG. 11A shows a waveform illustrating the fluctuation of the exhaust gas pressure in the vicinity of a gas-introducing port in Comparative Example.
Figure 11B:
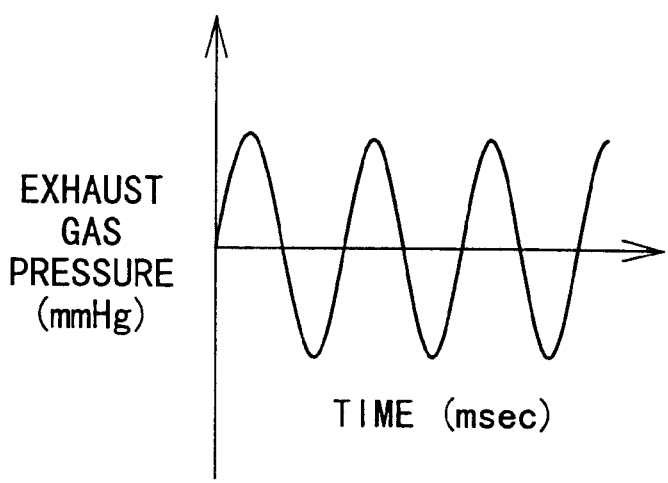
FIG. 11B shows a waveform illustrating the fluctuation of the exhaust gas pressure in the vicinity of an inlet of a first chamber.

The above result is obtained probably because of the following reason. That is, as shown in FIGS. 11A and 11B to depict waveforms, the fluctuation of the exhaust gas pressure in the vicinity of the gas-introducing port is approximately the same as the fluctuation of the exhaust gas pressure in the vicinity of the inlet of the first chamber 18, and the fluctuation of the exhaust gas pressure associated with the change in measurement condition directly affects the sensor output.

Figure 12A:
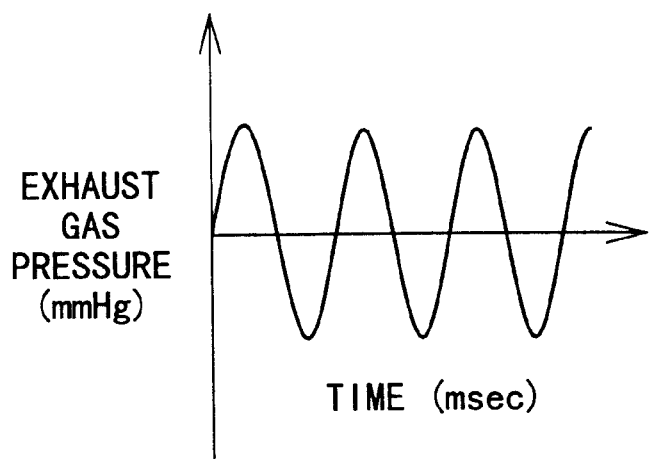
FIG. 12A shows a waveform illustrating the fluctuation of the exhaust gas pressure in the vicinity of a gas-introducing port in Working Example.
Figure 12B:
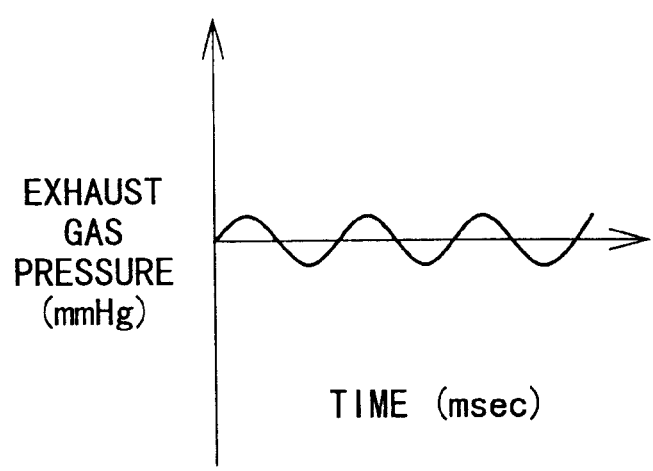
FIG. 12B shows a waveform illustrating the fluctuation of the exhaust gas pressure in the vicinity of an inlet of a first chamber.

On the other hand, in Working Example, the sensor output does not fluctuates as shown in FIGS. 9 and 10 even when the measurement condition is changed. It is possible to obtain the sensor output depending on the change in oxygen concentration and NOx concentration at a high degree of accuracy. This is probably because of the following reason. That is, as shown in FIGS. 12A and 12B to depict waveforms, the fluctuation of the exhaust gas pressure in the vicinity of the gas-introducing port is attenuated by the wall resistance of the first diffusion rate-determining section 26. Therefore, the fluctuation of the exhaust gas pressure in the vicinity of the inlet of the first chamber 18 is smaller than the fluctuation of the exhaust gas pressure in the vicinity of the gas-introducing port.

As described above, the gas sensor 10A according to the first embodiment makes it possible to avoid the influence of the pulsation of the exhaust gas pressure generated in the measurement gas. Thus, it is possible to improve the measurement accuracy obtained on the measuring pumping cell 64.

Next, explanation will be made with reference to FIGS. 13A to 30 for several modified embodiments of the gas sensor 10A according to the first embodiment, namely modified embodiments principally concerning the shape of the first diffusion rate-determining section 26 and the second diffusion rate-determining section 28. In FIGS. 13A to 30, the electric circuit system is omitted from the illustration in order to avoid complicated drawings. Components or parts corresponding to those shown in FIG. 1 are designated by the same reference numerals, duplicate explanation of which will be omitted.

Figure 13B:
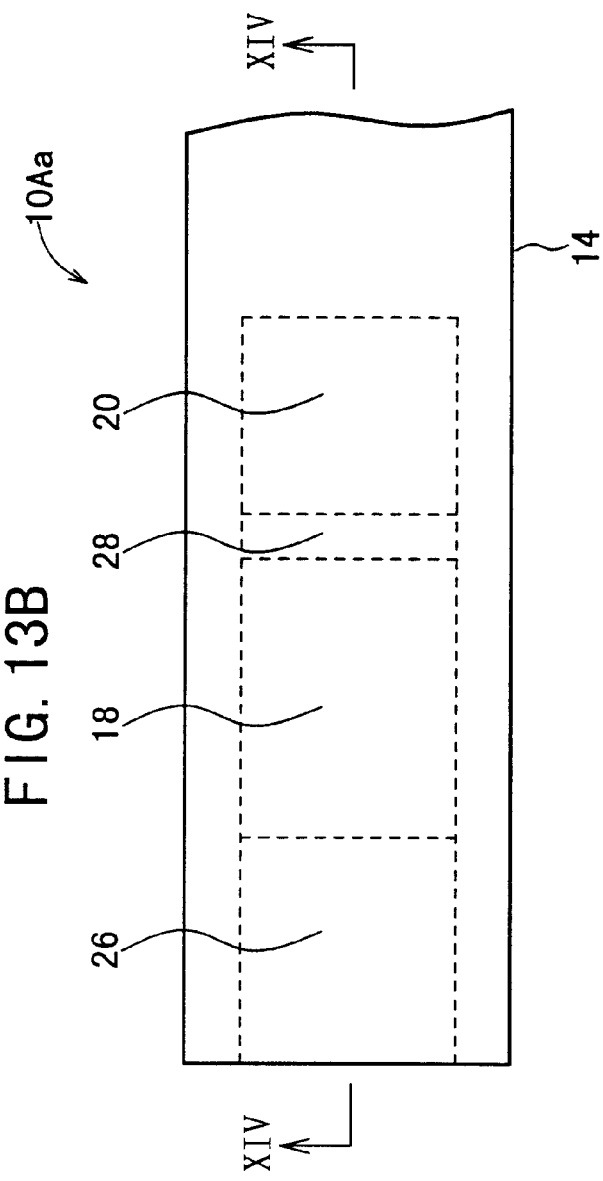
FIG. 13B shows a front view thereof.
Figure 13A:
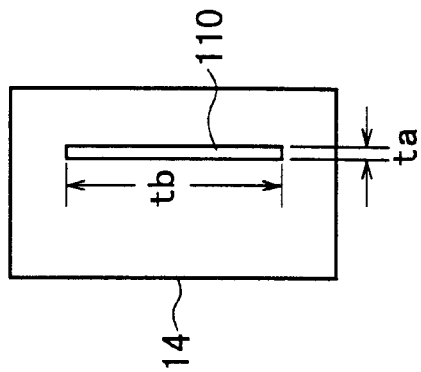
FIG. 13A shows a front view illustrating an arrangement of a gas sensor according to a first modified embodiment.

At first, as shown in FIGS. 13A, 13B, and 14, a gas sensor 10A*a* according to the first modified embodiment differs in that the first and second diffusion rate-determining sections 26, 28 are formed by single laterally extending slits 110, 112 respectively.

Specifically, the first diffusion rate-determining section 26 includes the slit 110 having a laterally extending aperture formed at a front end portion of the second spacer layer 12*e* to make contact with the upper surface of the first solid electrolyte layer 12*d*, the aperture being formed to extend with an identical aperture width up to the first chamber 18. The second diffusion rate-determining section 28 includes the slit 112 having an aperture formed at a terminal end portion of the first chamber 18 of the second spacer layer 12*e* to make contact with the upper surface of the first solid electrolyte layer 12*d*, the aperture being formed to extend with an identical aperture width up to the second chamber 20. In the first modified embodiment, each of the slits 110, 112 has approximately the same cross-sectional configuration, in which the length ta in the vertical direction is not more than 10 μm, and the length tb in the lateral direction is about 2 mm.

Figure 15B:
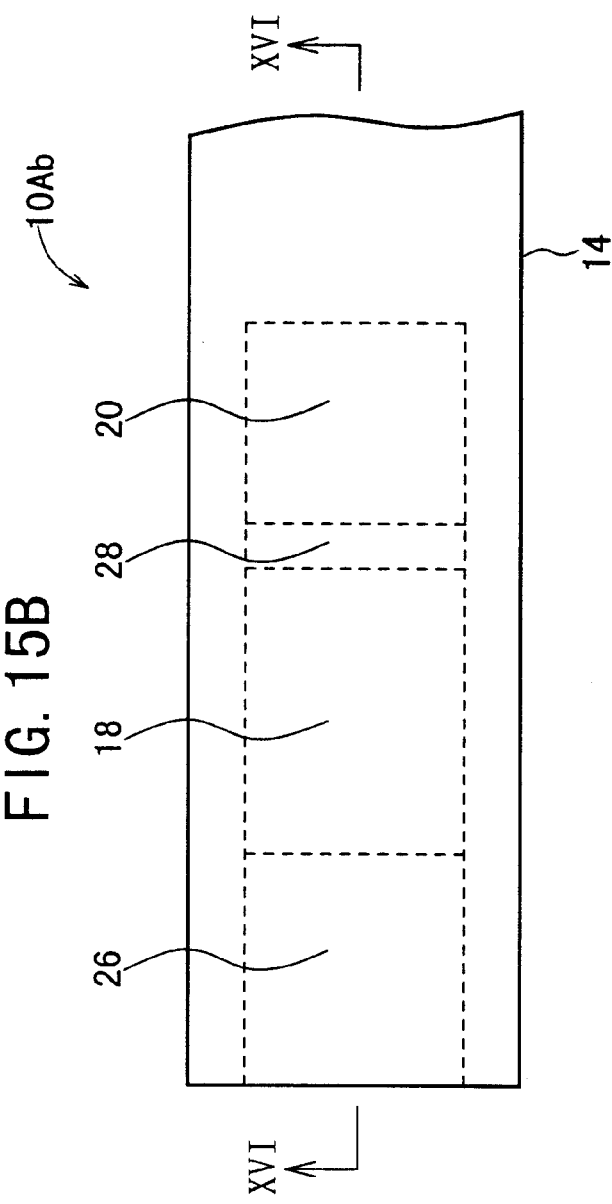
FIG. 15B shows a front view thereof.
Figure 15A:
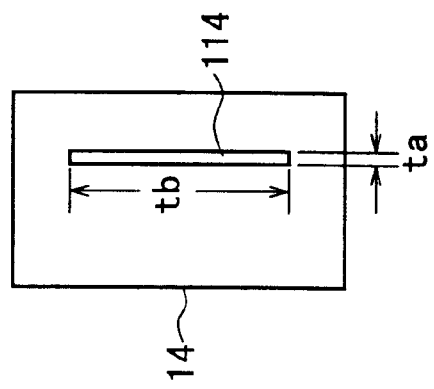
FIG. 15A shows a front view illustrating an arrangement of a gas sensor according to a second modified embodiment.
Figure 16:
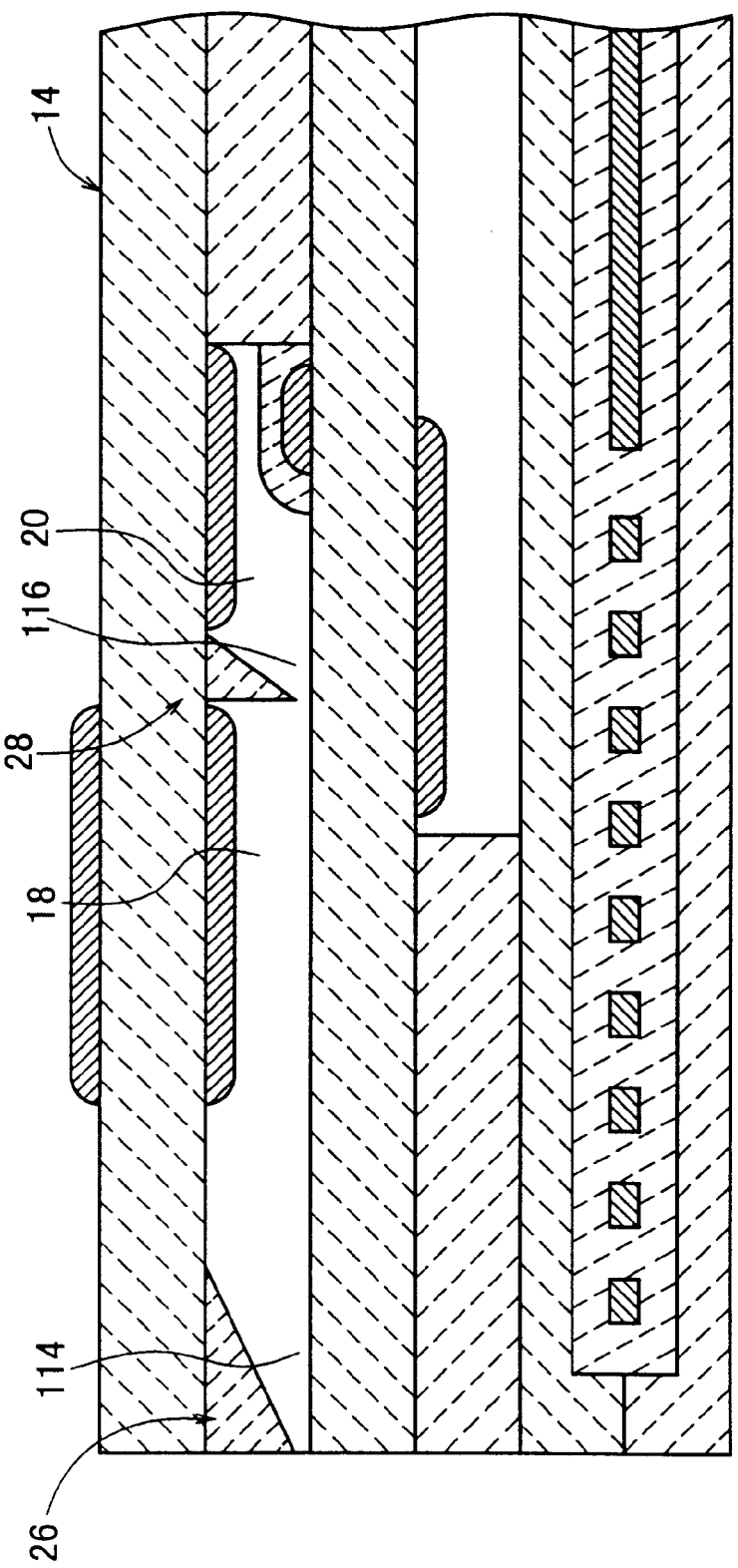
FIG. 16 shows a sectional view taken along a line XVI—XVI shown in FIG. 15B.

Next, as shown in FIGS. 15A, 15B, and 16, a gas sensor 10A*b* according to the second modified embodiment differs in that the first and second diffusion rate-determining sections 26, 28 are formed by single laterally extending wedge-shaped slits 114, 116 respectively.

Specifically, the first diffusion rate-determining section 26 includes the wedge-shaped slit 114 having a laterally extending aperture formed at a front end portion of the second spacer layer 12*e* to make contact with the upper surface of the first solid electrolyte layer 12*d*, the aperture being formed to extend with an aperture width (width in the vertical direction) gradually enlarged toward the first chamber 18. The second diffusion rate-determining section 28 includes the wedge-shaped slit 116 having a laterally extending aperture formed at a terminal end portion of the first chamber 18 of the second spacer layer 12*e* to make contact with the upper surface of the first solid electrolyte layer 12*d*, the aperture being formed to extend with an aperture width gradually enlarged toward the second chamber 20.

In the second modified embodiment, the minimum aperture at the front end of each of the wedge-shaped slits 114, 116 has approximately the same cross-sectional configuration, in which the length ta in the vertical direction is not more than 10 μm, and the length tb in the lateral direction is about 2 mm.

Figures 17A, 17B:
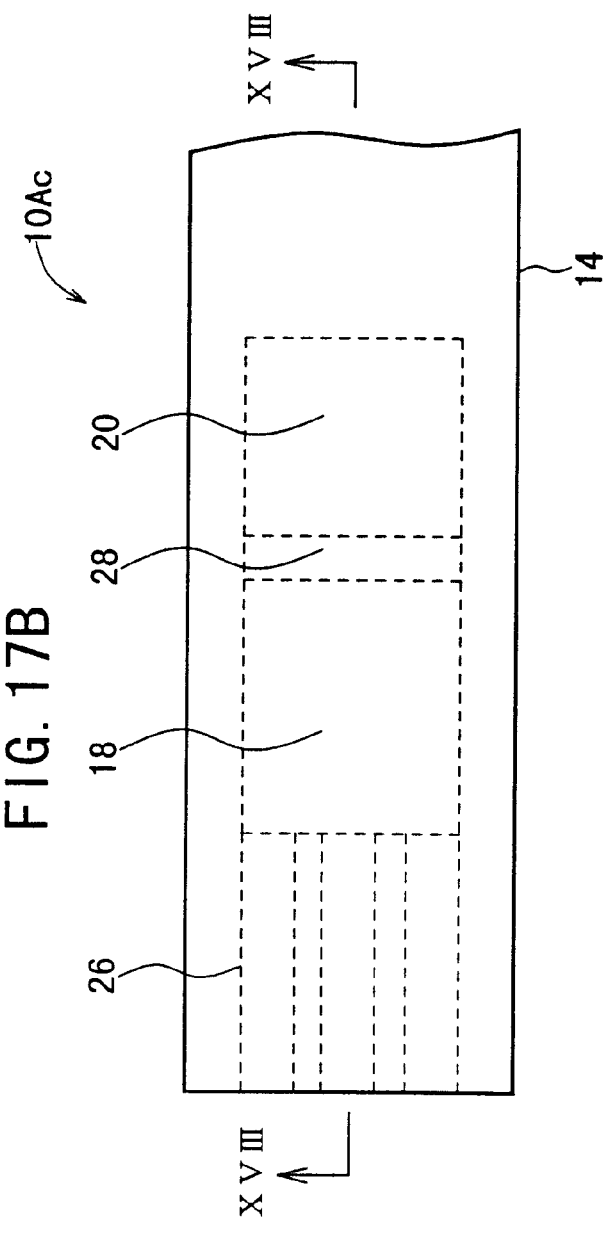
FIG. 17A shows a front view illustrating an arrangement of a gas sensor according to a third modified embodiment.
FIG. 17B shows a front view thereof.
Figure 18:
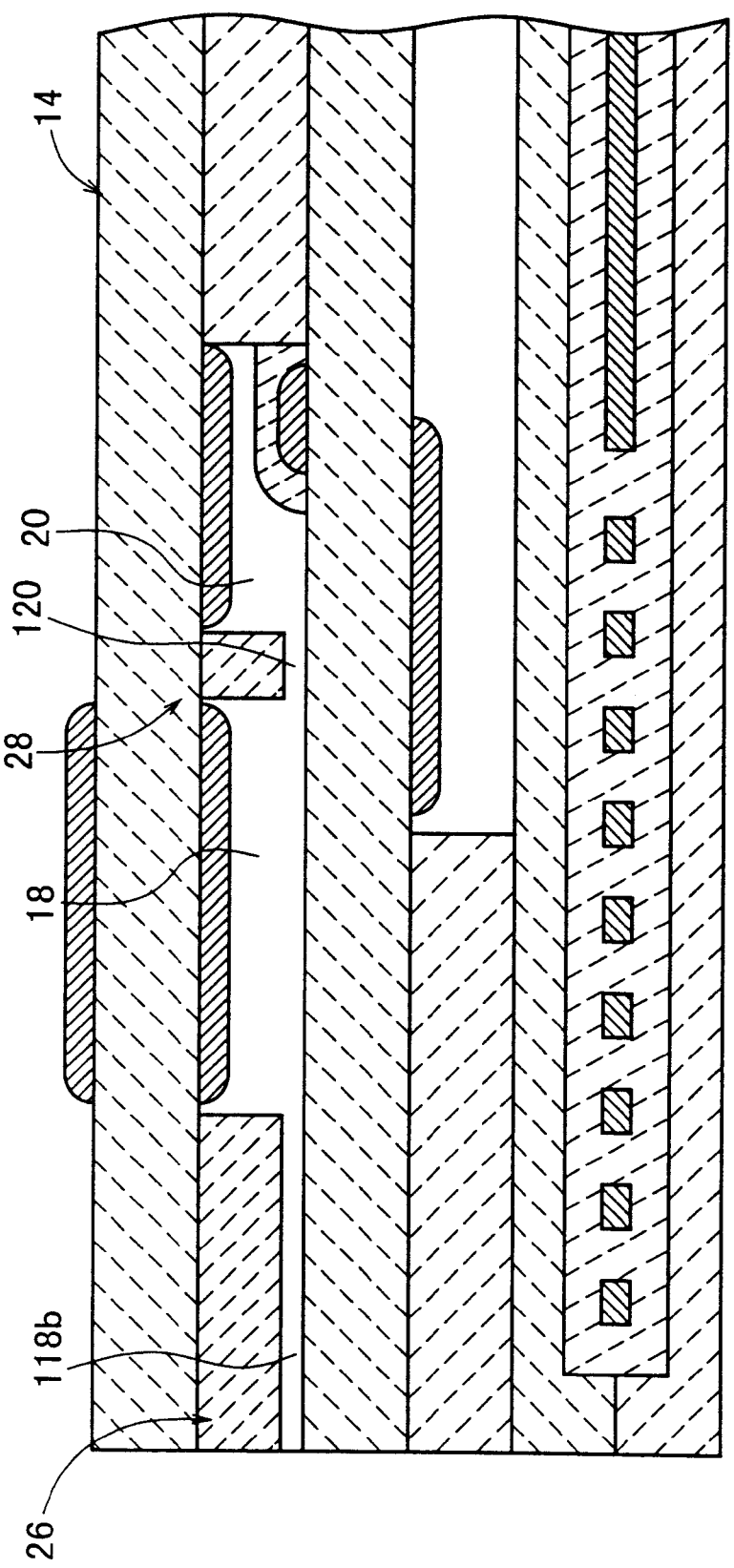
FIG. 18 shows a sectional view taken along a line XVIII—XVIII shown in FIG. 17B.

Next, as shown in FIGS. 17A, 17B, and 18, a gas sensor 10A*c* according to the third modified embodiment differs in that the first diffusion rate-determining section 26 is formed by three laterally extending slits 118*a*, 118*b*, 118*c* which are disposed in parallel to one another, and the second diffusion rate-determining section 28 is formed by a single laterally extending slit 120.

Specifically, the first diffusion rate-determining section 26 includes the three slits 118*a*, 118*b*, 118*c* having three laterally extending apertures formed in parallel to one another at front end portions of the second spacer layer 12*e* to make contact with the upper surface of the first solid electrolyte layer 12*d*, each of the apertures being formed to extend with an identical aperture width up to the first chamber 18. The second diffusion rate-determining section 28 includes the single slit 120 having a single laterally extending aperture formed at a terminal end portion of the first chamber 18 of the second spacer layer 12*e* to make contact with the upper surface of the first solid electrolyte layer 12*d*, the aperture being formed to extend with an identical aperture width up to the second chamber 20. In the third modified embodiment, each of the slits 118*a*, 118*b*, 118*c*, 120 has the length ta in the vertical direction which is not more than 10 μm.

Figure 19A:
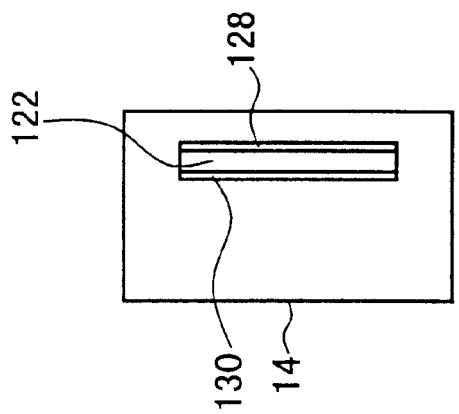
FIG. 19A shows a front view illustrating an arrangement of a gas sensor according to a fourth modified embodiment.
Figure 19B:
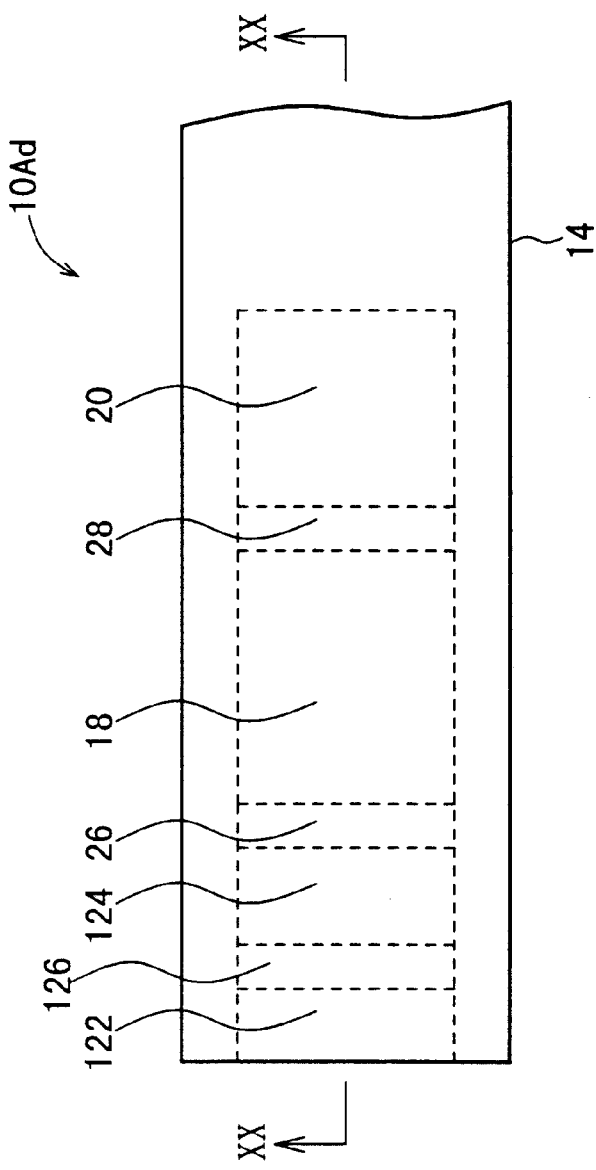
FIG. 19B shows a front view thereof.
Figure 20:
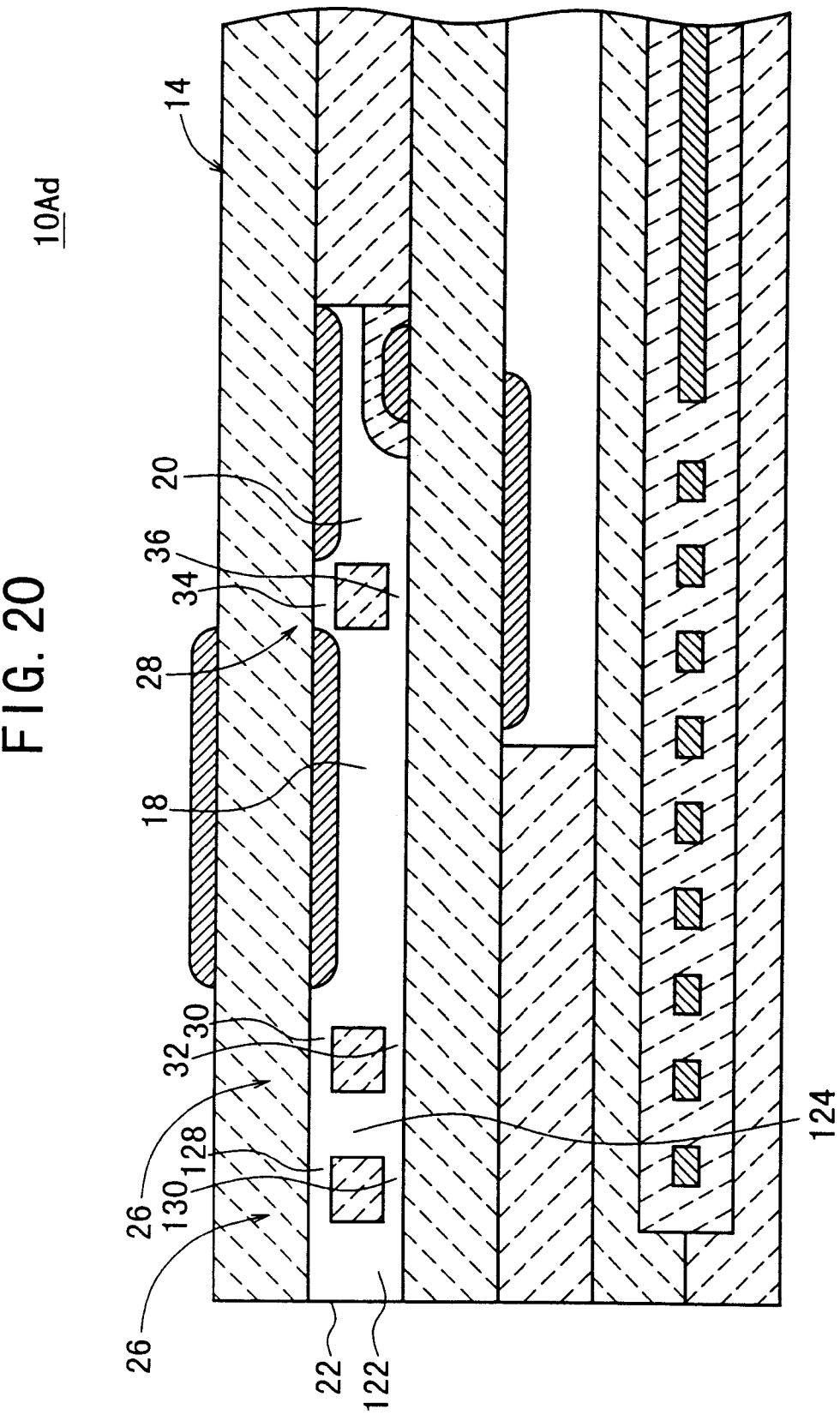
FIG. 20 shows a sectional view taken along a line XX—XX shown in FIG. 19B.

Next, as shown in FIGS. 19A, 19B, and 20, a gas sensor 10A*d* according to the fourth modified embodiment differs in that a space section 122 and a buffering space 124 are provided in series between the gas-introducing port 22 and the first diffusion rate-determining section 26, a front aperture of the space section 122 constitutes the gas-introducing port 22, and a fourth diffusion rate-determining section 126 for giving a predetermined diffusion resistance to the measurement gas is provided between the space section 122 and the buffering space 124.

Each of the first diffusion rate-determining section 26 and the second diffusion rate-determining section 28 is formed by two laterally extending slits 30, 32, 34, 36, in the same manner as in the gas sensor 10A according to the first embodiment.

The fourth diffusion rate-determining section 126 includes a slit 128 having a laterally extending aperture formed at a terminal end portion of the space section 122 of the second spacer layer 12*e* to make contact with the lower surface of the second solid electrolyte layer 12*f*, the aperture being formed to extend with an identical aperture width up to the buffering space 124. The fourth diffusion rate-determining section 126 further includes a slit 130 having a laterally extending aperture formed at a terminal end portion of the space section 122 of the second spacer layer 12e to make contact with the upper surface of the first solid electrolyte layer 12d, the aperture being formed to extend with an identical aperture width up to the buffering space 124.

Figure 21B:
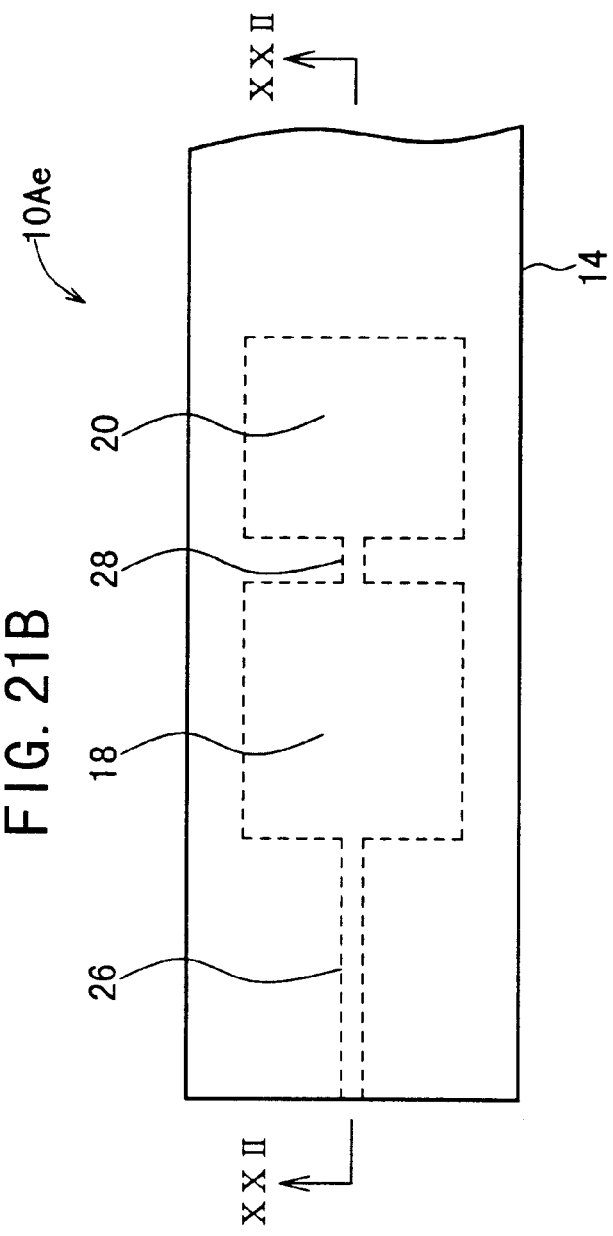
FIG. 21B shows a front view thereof.
Figure 21A:
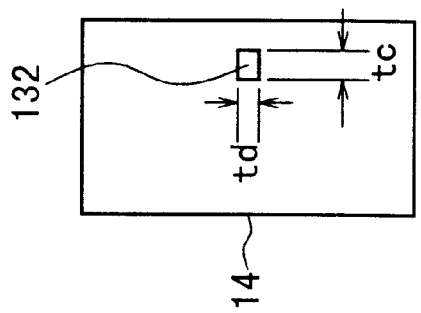
FIG. 21A shows a front view illustrating an arrangement of a gas sensor according to a fifth modified embodiment.
Figure 22:
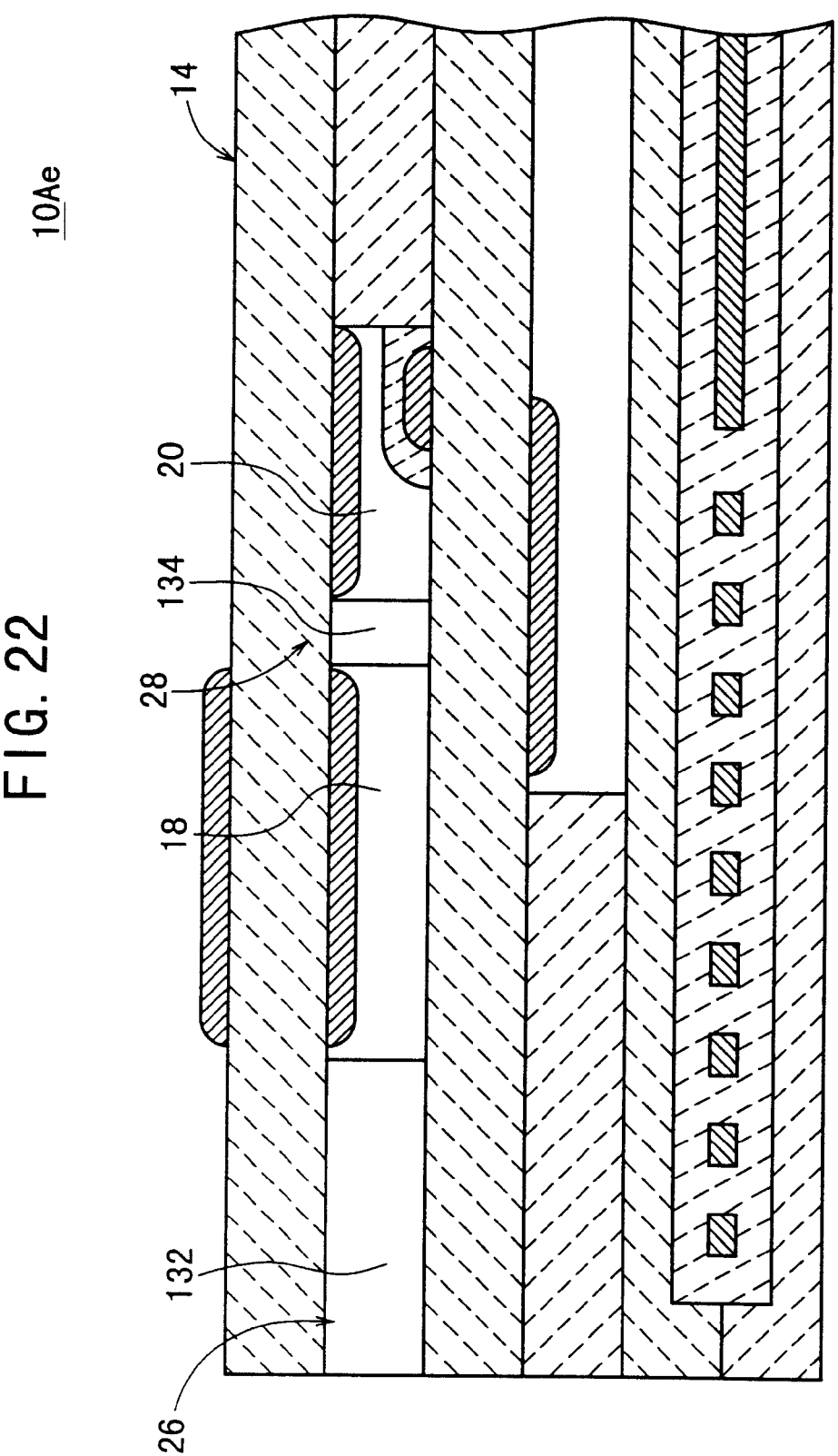
FIG. 22 shows a sectional view taken along a line XXII—XXII shown in FIG. 21B.

Next, as shown in FIGS. 21A, 21B, and 22, a gas sensor 10Ae according to the fifth modified embodiment differs in that each of the first and second diffusion rate-determining sections 26, 28 is formed by a single vertically extending slit 132, 134.

Specifically, the first diffusion rate-determining section 26 includes the slit 132 having a vertically extending aperture formed at a front end portion of the second spacer layer 12e approximately at the center in the widthwise direction thereof, the aperture being formed to extend with an identical aperture width up to the first chamber 18. The second diffusion rate-determining section 28 includes the slit 134 having a vertically extending aperture formed at a terminal end portion of the first chamber 18 of the second spacer layer 12e approximately at the center in the widthwise direction thereof, the aperture being formed to extend with an identical aperture width up to the second chamber 20. In the fifth modified embodiment, each of the slits 132, 134 has approximately the same cross-sectional configuration, in which the length tc in the vertical direction is the same as the thickness of the second spacer layer 12e, and the length td in the lateral direction is not more than 10 $\mu$m.

Figure 23B:
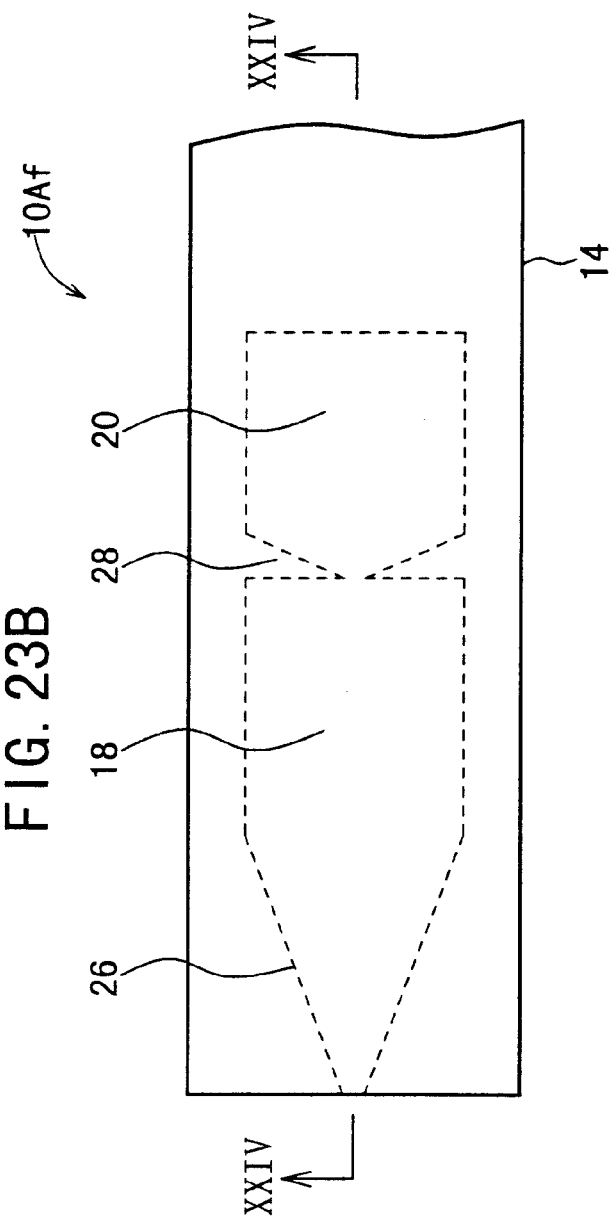
FIG. 23B shows a front view thereof.
Figure 23A:
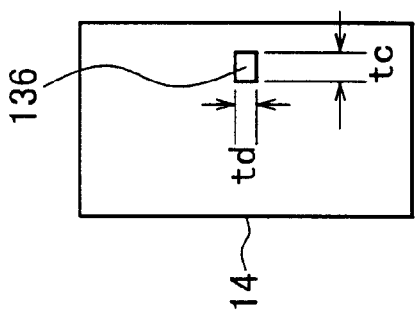
FIG. 23A shows a front view illustrating an arrangement of a gas sensor according to a sixth modified embodiment.
Figure 24:
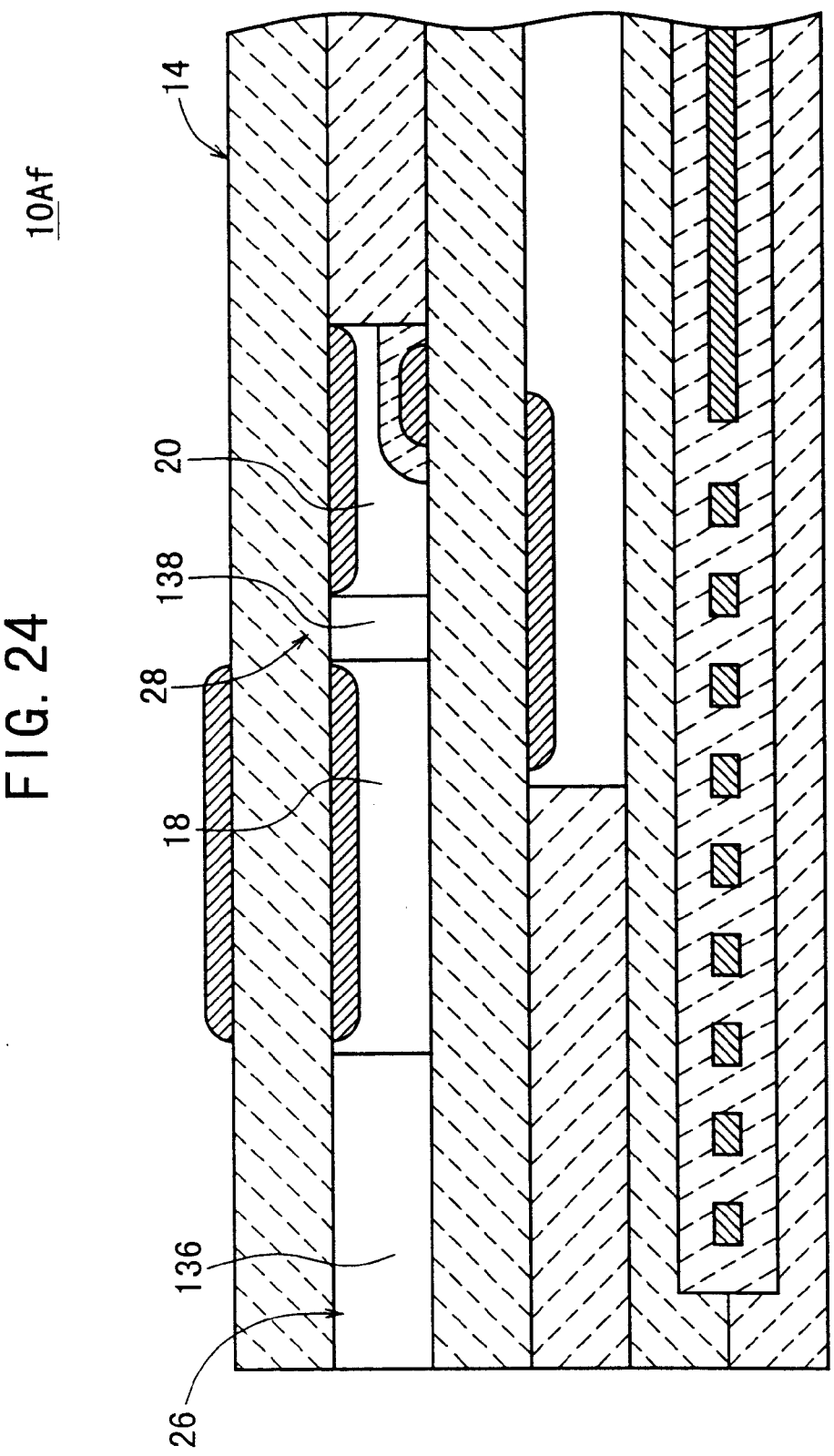
FIG. 24 shows a sectional view taken along a line XXIV—XXIV shown in FIG. 23B.

Next, as shown in FIGS. 23A, 23B, and 24, a gas sensor 10Af according to the sixth modified embodiment differs in that the first and second diffusion rate-determining sections 26, 28 are formed by single vertically extending wedge-shaped slits 136, 138 respectively.

Specifically, the first diffusion rate-determining section 26 includes the wedge-shaped slit 136 having a vertically extending aperture formed at a front end portion of the second spacer layer 12e approximately at the center in the widthwise direction thereof, the aperture being formed to extend with an aperture width (width in the lateral direction) gradually enlarged toward the first chamber 18. The second diffusion rate-determining section 28 includes the wedge-shaped slit 138 having a vertically extending aperture formed at a terminal end portion of the first chamber 18 of the second spacer layer 12e approximately at the center in the widthwise direction thereof, the aperture being formed to extend with an aperture width (width in the lateral direction) gradually enlarged toward the second chamber 20.

In the sixth modified embodiment, the minimum aperture at the front end of each of the wedge-shaped slits 136, 138 has approximately the same cross-sectional configuration, in which the length tc in the vertical direction is the same as the thickness of the second spacer layer 12e, and the length td in the lateral direction is not more than 10 $\mu$m.

Figure 25B:
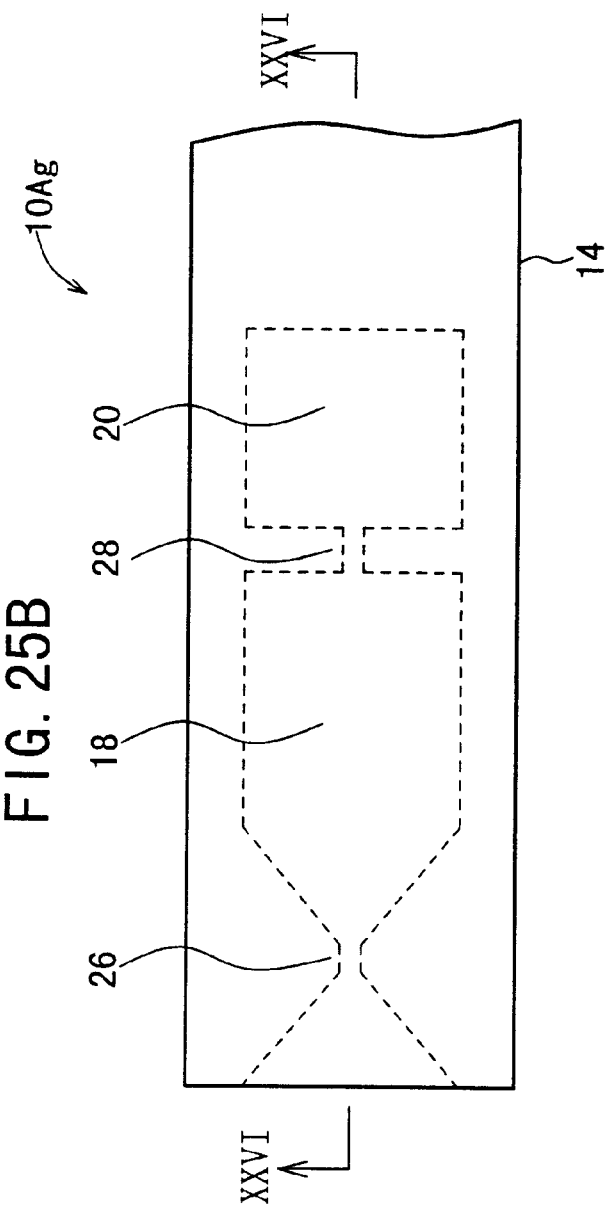
FIG. 25B shows a front view thereof.
Figure 25A:
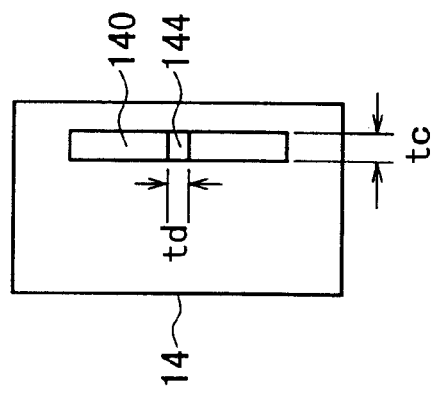
FIG. 25A shows a front view illustrating an arrangement of a gas sensor according to a seventh modified embodiment.
Figure 26:
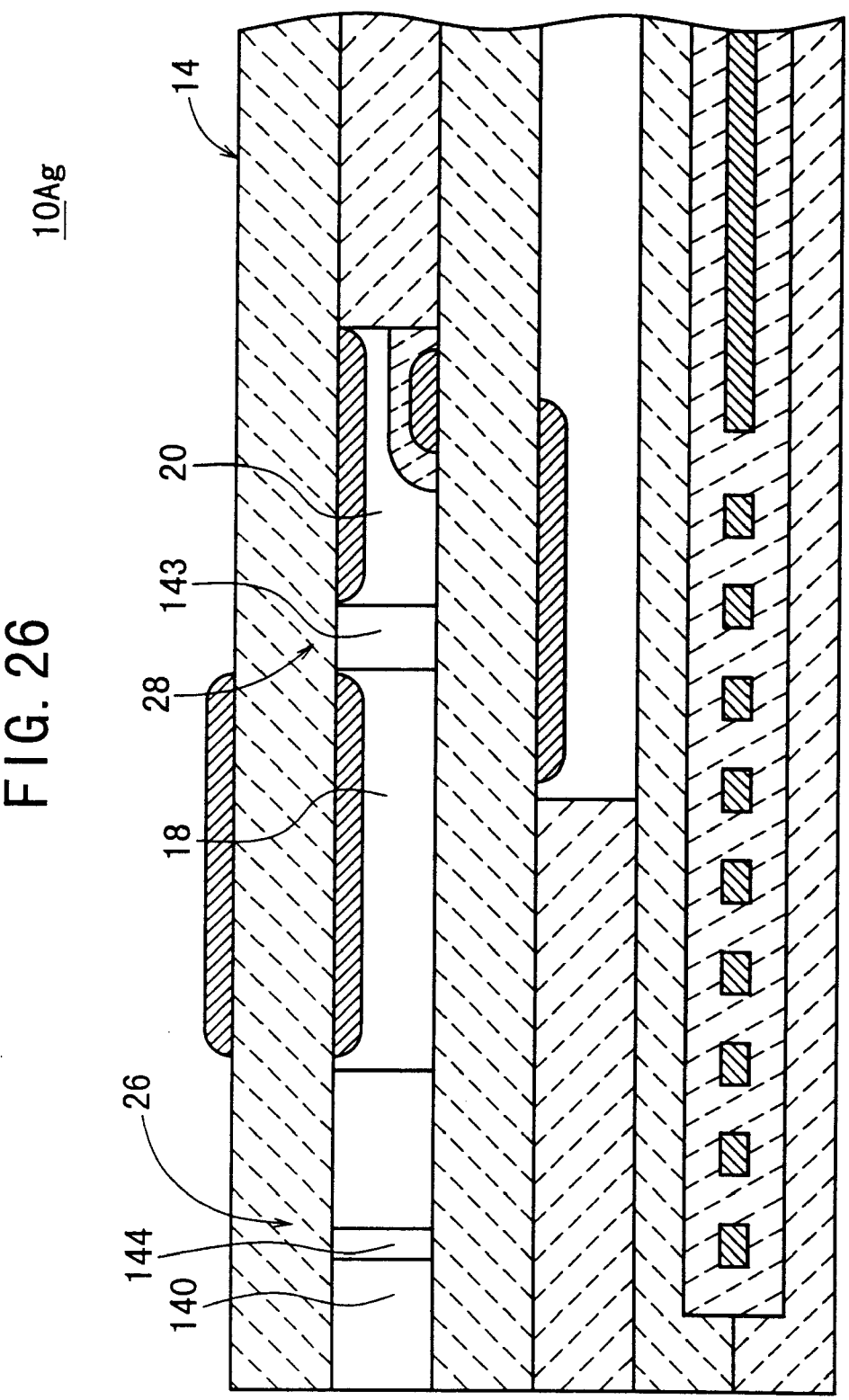
FIG. 26 shows a sectional view taken along a line XXVI—XXVI shown in FIG. 25B.

Next, as shown in FIGS. 25A, 25B, and 26, a gas sensor 10Ag according to the seventh modified embodiment differs in that the first diffusion rate-determining section 26 is formed by a slit 140 having a substantially hourglass-shaped planar configuration, and the second diffusion rate-determining section 28 is formed by a single vertically extending slit 142.

Specifically, the first diffusion rate-determining section 26 includes the substantially hourglass-shaped slit 140 starting from a laterally extending aperture formed at a front end portion of the second spacer layer 12e, the aperture having its aperture width (width in the lateral direction) gradually decreasing toward the approximate center of the first diffusion rate-determining section 26 in the depth direction to form a vertically extending slit 144, in which the aperture width (width in the lateral direction) of the slit 144 gradually increases toward the first chamber 18 to form the substantially hourglass-shaped slit 140.

On the other hand, the second diffusion rate-determining section 28 includes the slit 142 having a vertically extending aperture formed at a terminal end portion of the first chamber 18 of the second spacer layer 12e approximately at the center in the widthwise direction thereof, the aperture being formed to extend with an is identical aperture width up to the second chamber 20.

In the seventh modified embodiment, the minimum aperture (slit 144) of the hourglass-shaped slit 140 for constructing the first diffusion rate-determining section 26 has approximately the same cross-sectional configuration as that of the slit 142 for constructing the second diffusion rate-determining section 28, in which the length tc in the vertical direction is the same as the thickness of the second spacer layer 12e, and the length td in the lateral direction is not more than 10 $\mu$m.

Figure 27B:
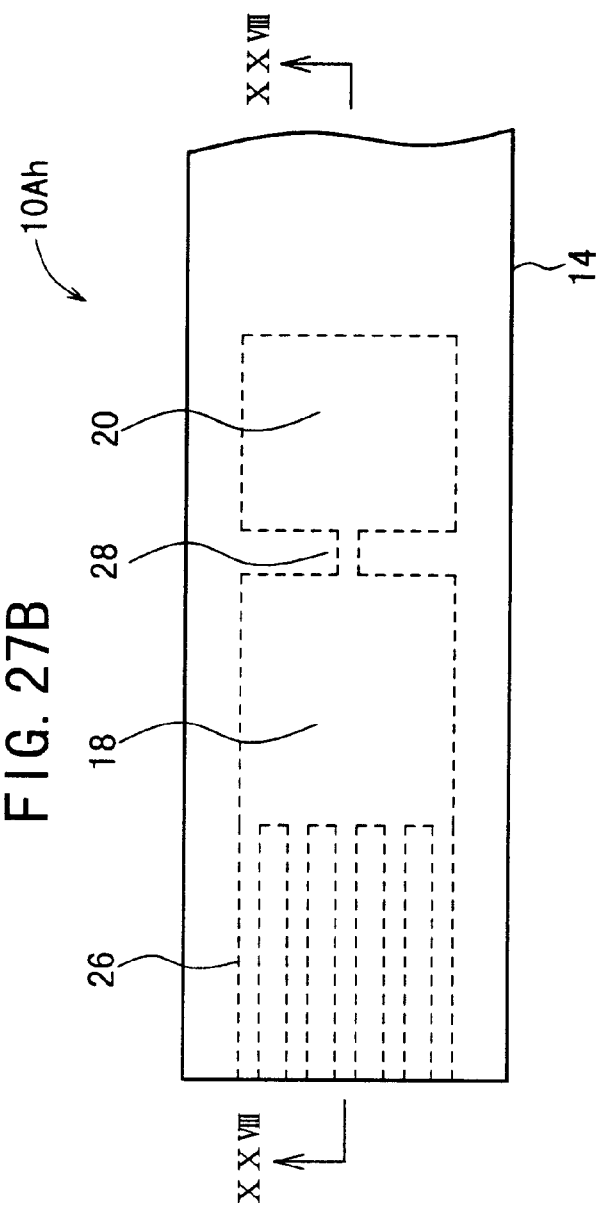
FIG. 27B shows a front view thereof.
Figure 27A:
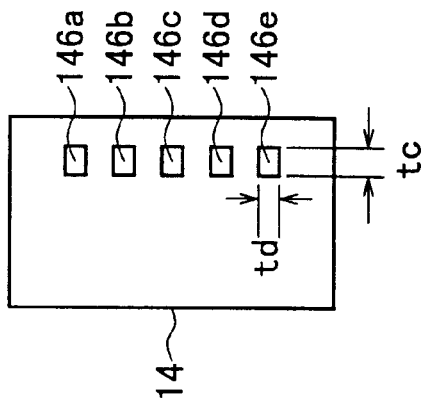
FIG. 27A shows a front view illustrating an arrangement of a gas sensor according to an eighth modified embodiment.
Figure 28:
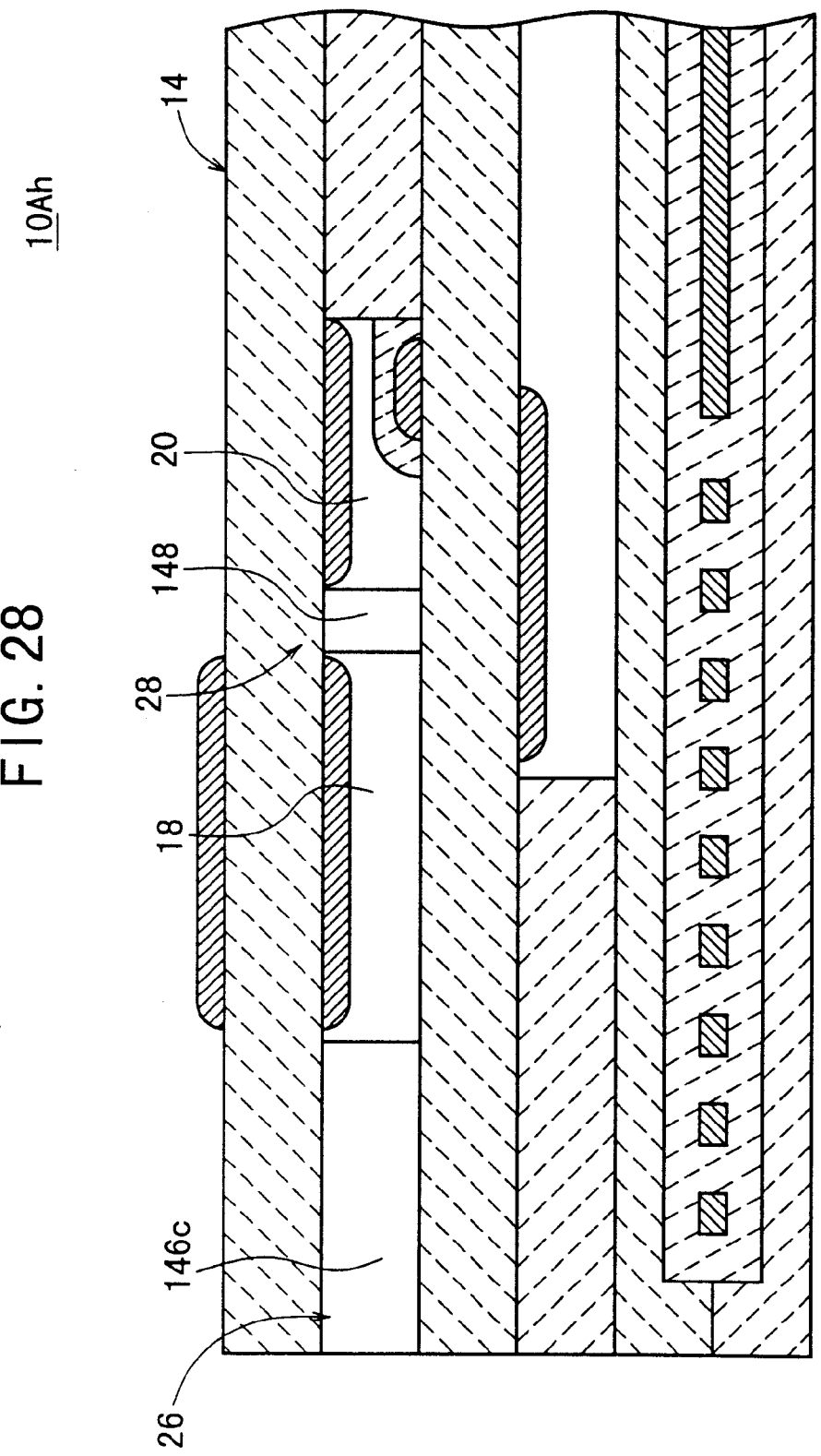
FIG. 28 shows a sectional view taken along a line XXVIII—XXVIII shown in FIG. 27B.

Next, as shown in FIGS. 27A, 27B, and 28, a gas sensor 10Ah according to the eighth modified embodiment differs in that the first diffusion rate-determining section 26 is formed by five vertically extending slits 146a to 146e which are disposed in parallel to one another, and the second diffusion rate-determining section 28 is formed by a single vertically extending slit 148.

Specifically, the first diffusion rate-determining section 26 includes the five slits 146a to 146e having five vertically extending apertures formed in parallel to one another at terminal end portions of the second spacer layer 12e, each of the apertures being formed to extend with an identical aperture width up to the first chamber 18. The second diffusion rate-determining section 28 includes the single slit 148 having a vertically extending aperture formed at a terminal end portion of the first chamber 18 of the second spacer layer 12e approximately at the center in the widthwise direction thereof, the aperture being formed to extend with an identical aperture width up to the second chamber 20. In the eighth modified embodiment, the length td in the lateral direction of each of the slits 146a to 146e, 148 is not more than 10 $\mu$m.

Figure 29B:
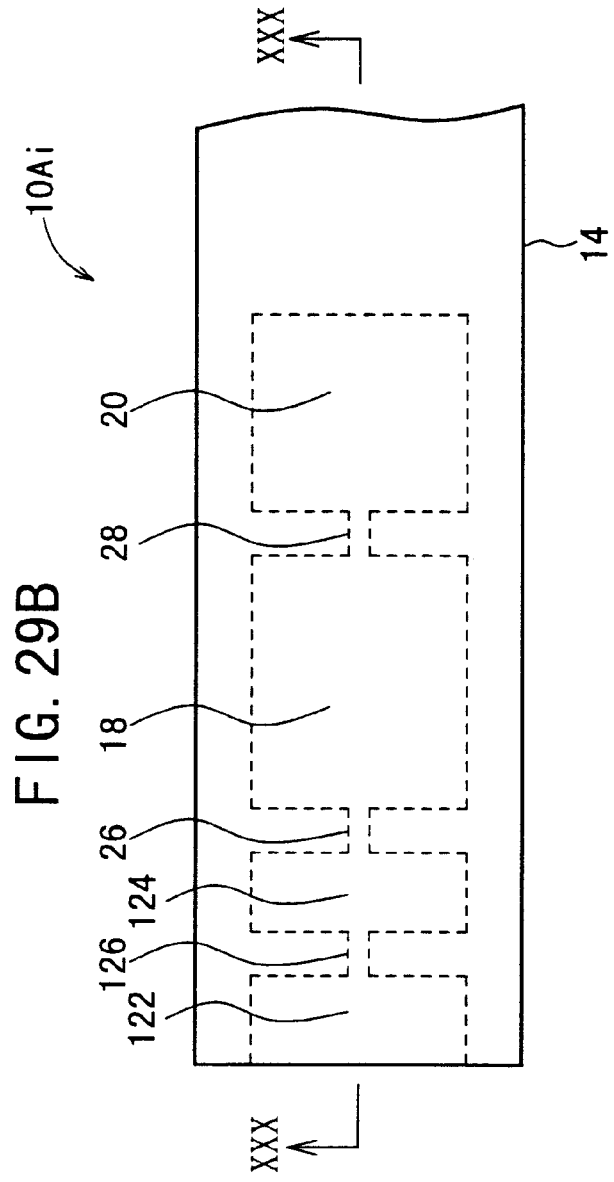
FIG. 29B shows a front view thereof.
Figure 29A:
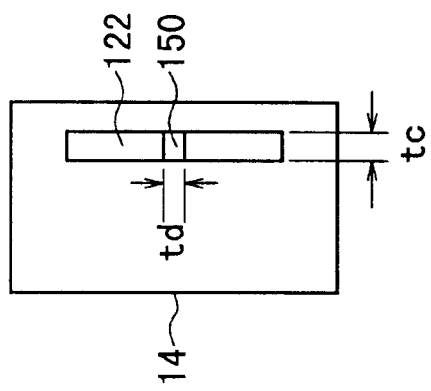
FIG. 29A shows a front view illustrating an arrangement of a gas sensor according to a ninth modified embodiment.

Next, as shown in FIGS. 29A, 29B, and 30, a gas sensor 10Ai according to the ninth modified embodiment differs in that a space section 122 and a buffering space 124 are provided in series between the gas-introducing port 22 and the first diffusion rate-determining section 26, a front aperture of the space section 122 constitutes the gas-introducing port 22, and a fourth diffusion rate-determining section 126 for giving a predetermined diffusion resistance to the measurement gas is provided between the space section 122 and the buffering space 124.

Each of the first diffusion rate-determining section 26 and the second diffusion rate-determining section 28 is formed by a single laterally extending slit 132, 134, in the same manner as in the gas sensor 10Ae according to the fifth modified embodiment (see FIGS. 21A, 21B, and 22).

The fourth diffusion rate-determining section 126 includes a slit 150 having a vertically extending aperture formed at a terminal end portion of the space section 122 of the second spacer layer 12e approximately at the center in the widthwise direction thereof, the aperture being formed to extend with an identical aperture width up to the buffering space 124.

The gas sensors 10Aa to 10Ai according to the first to ninth modified embodiments make it possible to avoid the influence of the pulsation of the exhaust gas pressure generated in the measurement gas, in the same manner as the gas sensor 10A according to the first embodiment. Thus, it is possible to improve the measurement accuracy obtained on the measuring pumping cell 64.

Especially, the gas sensors 10Ad and 10Ai according to the fourth and ninth modified embodiments include the buffering space 124 provided at the upstream stage of the first diffusion rate-determining section 26. Usually, the oxygen suddenly enters the sensor element 14 via the gas-introducing port 22 due to the pulsation of the exhaust gas pressure in the external space. However, in this arrangement, the oxygen from the external space does not directly enter the processing space, but it enters the buffering space 124 disposed at the upstream stage thereof. In other words, the sudden change in oxygen concentration, which is caused by the pulsation of the exhaust gas pressure, is counteracted by the buffering space 124. Thus, the influence of the pulsation of the exhaust gas pressure on the first chamber 18 is in an almost negligible degree.

As a result, the correlation is improved between the oxygen-pumping amount effected by the main pumping cell 44 for the first chamber 18 and the oxygen concentration in the measurement gas. It is possible to improve the measurement accuracy obtained by the measuring pumping cell 64. Simultaneously, for example, it is possible to concurrently use the first chamber 18 as a sensor for determining the air-fuel ratio.

The gas sensors 10Ad and 10Ai according to the fourth and ninth modified embodiment described above include the space section 122 and the buffering space 124 which are provided in series between the gas-introducing port 22 and the first diffusion rate-determining section 26, and the front aperture of the space section 122 is used to form the gas-introducing port 22. The space section 122 functions as the clogging-preventive section for avoiding the clogging of particles (for example, soot and oil combustion waste) produced in the measurement gas in the external space, which would be otherwise caused in the vicinity of the inlet of the buffering space 124. Accordingly, it is possible to measure the NOx component more accurately by using the measuring pumping cell 64. Further, it is possible to maintain a highly accurate state over a long period of time.

The gas sensor 10A according to the first embodiment and the gas sensors 10Aa to 10Ad according to the first to fourth modified embodiments described above have their first and second diffusion rate-determining sections 26, 28 each of which is constructed by the laterally extending slit. The gas sensors 10Ae to 10Ai according to the fifth to ninth modified embodiments have their first and second diffusion rate-determining sections 26, 28 each of which is constructed by the vertically extending slit. However, for example, the first diffusion rate-determining section 26 may be constructed by a laterally extending slit, and the second diffusion rate-determining section 28 may be constructed by a vertically extending slit. Alternatively, it is also allowable to adopt an arrangement in which the first and second diffusion rate-determining sections 26, 28 are constructed in an inverse manner of the above.

It is also allowable that the shape of each of the first and second diffusion rate-determining sections 26, 28 is not the slit-shaped configuration provided that the certain factor for constructing the cross-sectional area is not more than 10 µm. For example, an equivalent effect can be obtained such that a sublimable fiber is embedded, and a cylindrical diffusion rate-determining section having a diameter of not more than 10 µm is constructed after the sintering.

Next, a gas sensor 10B according to the second embodiment will be explained with reference to FIG. 31. Components or parts corresponding to those shown in FIG. 2 are designated by the same reference numerals, duplicate explanation of which will be omitted.

Figure 31:
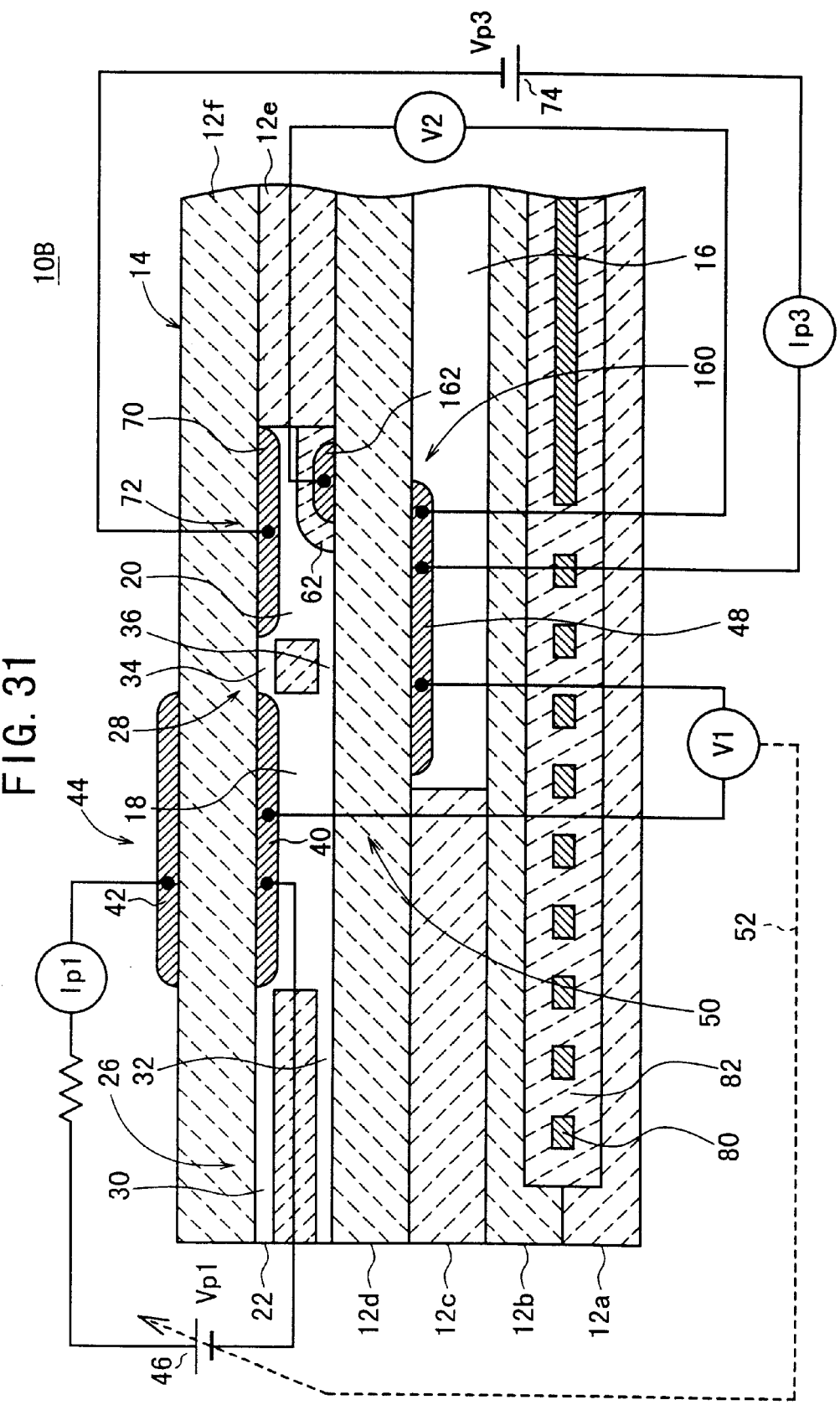
FIG. 31 shows a sectional view illustrating an arrangement of a gas sensor according to a second embodiment.
Figure 32:
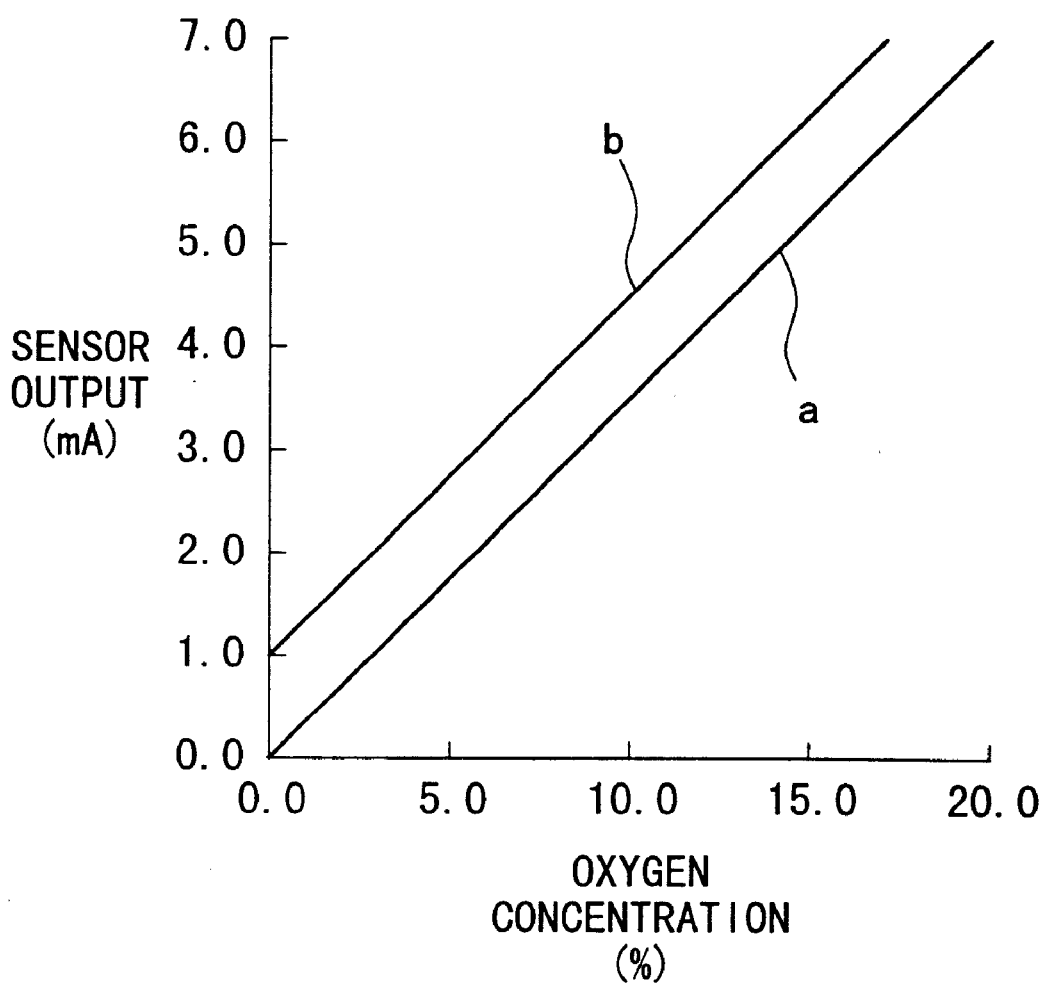
FIG. 32 shows the characteristic illustrating the change in sensor output with respect to the oxygen concentration concerning the conventional gas sensor.
Figure 33:
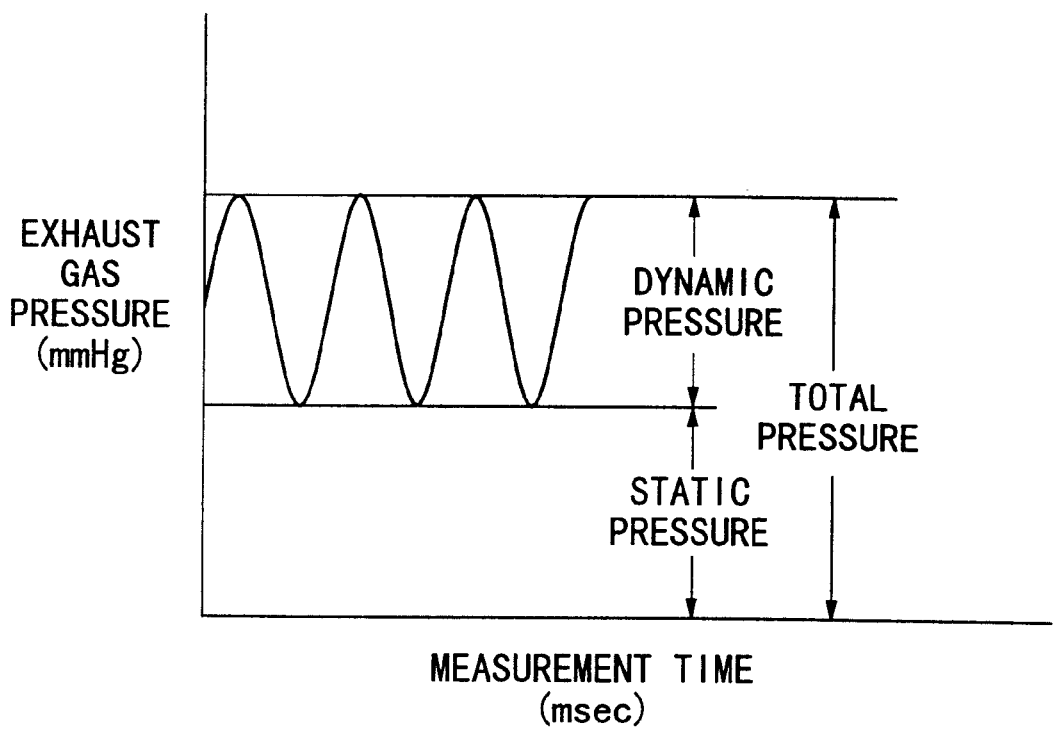
FIG. 33 illustrates the total pressure of the exhaust gas discharged from the automobile engine.

As shown in FIG. 31, the gas sensor 10B according to the second embodiment is constructed in approximately the same manner as the gas sensor 10A according to the first embodiment (see FIG. 2). However, the former is different from the latter in that a measuring oxygen partial pressure-detecting cell 160 is provided in place of the measuring pumping cell 64.

The measuring oxygen partial pressure-detecting cell 160 comprises a detecting electrode 162 formed on an upper surface portion for forming the second chamber 20, of the upper surface of the first solid electrolyte layer 12d, the reference electrode 48 formed on the lower surface of the first solid electrolyte layer 12d, and the first solid electrolyte layer 12d interposed between the both electrodes 162, 48.

In this embodiment, an electromotive force (electromotive force of an oxygen concentration cell) V2 corresponding to the difference in oxygen concentration between the atmosphere around the detecting electrode 162 and the atmosphere around the reference electrode 48 is generated between the reference electrode 48 and the detecting electrode 162 of the measuring oxygen partial pressure-detecting cell 160.

Therefore, the partial pressure of oxygen in the atmosphere around the detecting electrode 162, in other words, the partial pressure of oxygen defined by oxygen produced by reduction or decomposition of the measurement gas component (NOx) is detected as a voltage value V2 by measuring the electromotive force (voltage) V2 generated between the detecting electrode 162 and the reference electrode 48 by using a voltmeter 164.

Also in the gas sensor 10B according to the second embodiment, the pulsation (=dynamic pressure) of the exhaust gas pressure is attenuated by the wall resistance of the first diffusion rate-determining section 26. Therefore, it is possible to effectively suppress the shift-up phenomenon of the sensor output (pumping current value obtained by using the measuring pumping cell) which would be otherwise caused by the fluctuation of the dynamic pressure. As a result, it is possible to avoid the influence of the pulsation of the exhaust gas pressure generated in the measurement gas. It is possible to improve the measurement accuracy concerning the measuring oxygen partial pressure-detecting cell 160.

The arrangements of the gas sensors 10Aa to 10Ai according to the first to ninth modified embodiments can be also adopted to the gas sensor 10B according to the second embodiment.

The gas sensors 10A and 10B according to the first and second embodiments described above (including the respective modified embodiments) are directed to oxygen and NOx as the measurement gas component to be measured. However, the present invention is also effectively applicable to the measurement of bound oxygen-containing gas components such as $H_2O$ and $CO_2$ other than NOx, in which the measurement is affected by oxygen existing in the measurement gas.

For example, the present invention is also applicable to gas sensors which are constructed to pump out $O_2$ produced by electrolysis of $CO_2$ or $H_2O$ by using the oxygen pump, and to gas sensors in which $H_2$ produced by electrolysis of $H_2O$ is pumping-processed by using a proton ion-conductive solid electrolyte.

It is a matter of course that the gas sensor and the nitrogen oxide sensor according to the present invention are not limited to the embodiments described above, which may be embodied in other various forms without deviating from the gist or essential characteristics of the present invention.

As described above, according to the gas sensor and the nitrogen oxide sensor concerning the present invention, it is possible to avoid the influence of the pulsation of the exhaust gas pressure generated in the measurement gas, and it is possible to improve the measurement accuracy obtained on the detecting electrode.

What is claimed is:

1. A gas sensor for measuring an amount of a measurement gas component contained in a measurement gas existing in an external space, said gas sensor at least comprising:
   a substrate composed of a solid electrolyte to make contact with the external space;
   an internal space formed at the inside of said substrate;
   a gas-introducing port for introducing measurement gas from the external space into said internal space;
   a diffusion rate-determining slit passage for introducing measurement gas from the external space into said internal space via said gas-introducing port under a predetermined diffusion resistance;
   a buffering space provided between said gas-introducing port and said slit passage; and
   a pumping means including an inner pumping electrode and an outer pumping electrode formed at the inside and outside of said internal space respectively, for pumping-processing oxygen contained in the measurement gas introduced from the external space, on the basis of a control voltage applied between said electrodes, wherein:
      said slit passage has, when viewed in a plane substantially perpendicular to a longitudinal extension axis thereof, two dimensions, and at least one dimension is not more than 10 $\mu$m; and
      said buffering space has a cross-sectional area greater than that of said slit passage.

2. The gas sensor according to claim 1, wherein:
   a clogging-preventative section and said buffering space are provided in series between said gas-introducing port and said internal space;
   a front aperture of said clogging-preventive section is used to form said gas-introducing port; and
   a diffusion rate-determining section for giving a predetermined diffusion resistance to said measurement gas is provided between said clogging-preventive section and said buffering space.

3. The gas sensor according to claim 1, wherein said oxygen contained in the measurement gas introduced from said external space into the internal space is pumping-processed by using said pumping means to make control so that a partial pressure of oxygen in said internal space has a predetermined value at which a predetermined gas component in the measurement gas is not decomposable.

4. The gas sensor according to claim 3, further comprising:
   a measuring pumping means for decomposing said predetermined gas component contained in the measurement gas after being pumping-processed by said pumping means, by means of catalytic action and/or electrolysis, and pumping processing oxygen produced by said decomposition, wherein:
      the predetermined gas component contained in said measurement gas is measured on the basis of a pumping current flowing through said measuring pumping means in accordance with said pumping process effected by said measuring pumping means.

5. The gas sensor according to claim 3, further comprising:
   an oxygen partial pressure-detecting means for decomposing said predetermined gas component contained in the measurement gas after being pumping-processed by said pumping means, by means of catalytic action, and generating an electromotive force corresponding to a difference between an amount of oxygen produced by said decomposition and an amount of oxygen contained in a reference gas, wherein:
      the predetermined gas component contained in said measurement gas is measured on the basis of said electromotive force detected by said oxygen partial pressure-detecting means.

6. The gas sensor according to claim 1, wherein said substrate is substantially planar and said at least one dimension of said slit passage extends generally perpendicular to the plane of said substrate.

7. The gas sensor according to claim 1, wherein said substrate is substantially planar and said at least one dimension of said slit passage extends generally within the plane of said substrate.

8. A nitrogen oxide sensor for measuring an amount of a nitrogen oxide component contained in a measurement gas existing in an external space, said nitrogen oxide sensor at least comprising:
   a substrate composed of an oxygen ion-conductive solid electrolyte to make contact with the external space;
   a first internal space formed at the inside of said substrate and communicating with the external space;
   a gas-introducing port for introducing measurement gas from the external space into said first internal space;
   a first diffusion rate-determining slit passage for introducing the measurement gas into said first internal space via said gas-introducing port under a predetermined diffusion resistance;
   a clogging-preventive section provided between said gas-introducing port and said slit passage; and
   a main pumping means including a first inner pumping electrode and a first outer pumping electrode formed at the inside and outside of said first internal space respectively, for pumping-processing oxygen contained in the measurement gas introduced from said external space, on the basis of a control voltage applied between said electrodes so that a partial pressure of oxygen in said first internal space is controlled to have a predetermined value at which NO is not substantially decomposable;
   a second internal space communicating with said first internal space;
   a second diffusion rate-determining slit passage for introducing an atmosphere pumping-processed in said first internal space into said second internal space under a predetermined diffusion resistance; and
   a measuring pumping means including a second inner pumping electrode and a second outer pumping electrode formed at the inside and outside of said second internal space respectively, for decomposing NO contained in said atmosphere introduced from said first internal space, by means of catalytic action and/or electrolysis to pumping-process oxygen produced by said decomposition, wherein:
      said amount of nitrogen oxide contained in the measurement gas is measured on the basis of a pumping current flowing through said measuring pumping means in accordance with said pumping process effected by said measuring pumping means;

at least one of said first and second slit passages has, when viewed in a plane substantially perpendicular to longitudinal extension axes thereof, two dimensions, and at least one dimension is not more than 10 $\mu$m; and said clogging-preventive section has a cross-sectional area greater than that of said slit passage.

9. A nitrogen oxide sensor for measuring an amount of a nitrogen oxide component contained in a measurement gas existing in an external space, said nitrogen oxide sensor at least comprising:

a substrate composed of an oxygen ion-conductive solid electrolyte to make contact with the external space;

a first internal space formed at the inside of said substrate and communicating with the external space;

a gas-introducing port for introducing measurement gas from the external space into said first internal space;

a first diffusion rate-determining slit passage for introducing the measurement gas into said first internal space via said gas-introducing port under a predetermined diffusion resistance;

a clogging-preventive section provided between said gas-introducing port and said slit passage; and a main pumping means including an inner pumping electrode and an outer pumping electrode formed at the inside and outside of said first internal space respectively, for pumping-processing oxygen contained in the measurement gas introduced from said external space, on the basis of a control voltage applied between said electrodes so that a partial pressure of oxygen in said first internal space is controlled to have a predetermined value at which NO is not substantially decomposable;

a second internal space communicating with said first internal space;

a second diffusion rate-determining slit passage for introducing an atmosphere pumping-processed in said first internal space into said second internal space under a predetermined diffusion resistance; and an oxygen partial pressure-detecting means including an inner measuring electrode and an outer measuring electrode formed at the inside and outside of said second internal space respectively, for decomposing NO contained in said atmosphere introduced from said first internal space, by means of catalytic action to generate an electromotive force corresponding to a difference between an amount of oxygen produced by said decomposition and an amount of oxygen contained in a reference gas, wherein:

said amount of nitrogen contained in the measurement gas is measured on the basis of said electromotive force detected by said oxygen partial pressure-detecting means;

at least one of said first and second slit passages has, when viewed in a plane substantially perpendicular to longitudinal extension axes thereof, two dimensions, and at least one dimension is not more than 10 $\mu$m; and said clogging-preventive section has a cross-sectional area greater than that of said slit passage.

10. A gas sensor for measuring an amount of a measurement gas component contained in a measurement gas existing in an external space, said gas sensor at least comprising:

a substrate composed of a solid electrolyte to make contact with the external space;

an internal space formed at the inside of said substrate;

a gas-introducing port for allowing gas communication between the internal and external spaces;

a clogging-preventive section positioned adjacent said gas-introducing port and having at least one dimension substantially the same as that of said internal space;

a diffusion rate-determining slit passage for introducing the measurement gas from the external space via the gas-introducing port under a predetermined diffusion resistance; and a pumping means including an inner pumping electrode and an outer pumping electrode formed at the inside and outside of said internal space respectively, for pumping processing oxygen contained in the measurement gas introduced from the external space, on the basis of a control voltage applied between said electrodes, wherein:

said slit passage has, when viewed in a plane substantially perpendicular to a longitudinal extension axis thereof, two dimensions, and at least one dimension is not more than 10 $\mu$m; and said clogging-preventive section has a cross-sectional area greater than that of said slit passage.

* * * * *